US012740813B2

(12) United States Patent
Lopez Camacho et al.

(10) Patent No.: US 12,740,813 B2
(45) Date of Patent: Sep. 22, 2026

(54) EXTRAMEDULLARY DEVICE

(71) Applicant: Nuvasive Specialized Orthopedics, Inc., San Diego, CA (US)

(72) Inventors: Jorge Lopez Camacho, Oxnard, CA (US); Shawn Placie, Aliso Viejo, CA (US); Nathan Meyer, Vista, CA (US); Emmon Chen, Aliso Viejo, CA (US); Gabriel Buenviaje, Laguna Hills, CA (US); Woong Kim, Fresno, CA (US)

(73) Assignee: Globus Medical Inc., Audubon, PA (US)

( * ) Notice: Subject to any disclaimer, the term of this patent is extended or adjusted under 35 U.S.C. 154(b) by 908 days.

(21) Appl. No.: 17/971,044

(22) Filed: Oct. 21, 2022

(65) Prior Publication Data

US 2024/0130765 A1 Apr. 25, 2024
US 2024/0225704 A9 Jul. 11, 2024

(51) Int. Cl.
*A61B 17/80* (2006.01)
*A61B 17/68* (2006.01)

(52) U.S. Cl.
CPC .... *A61B 17/8004* (2013.01); *A61B 2017/681* (2013.01)

(58) Field of Classification Search
CPC ........ A61B 17/60; A61B 17/66; A61B 17/663; A61B 17/666; A61B 2017/681; A61B 17/8866
See application file for complete search history.

(56) References Cited

U.S. PATENT DOCUMENTS

| | | | |
|---|---|---|---|
| 2,702,031 | A | 2/1955 | Wenger |
| 3,111,945 | A | 11/1963 | Von Solbrig |
| 3,372,476 | A | 3/1968 | Peiffer |
| 3,377,576 | A | 4/1968 | Langberg |
| 3,512,901 | A | 5/1970 | Law |
| 3,597,781 | A | 8/1971 | Eibes |
| 3,900,025 | A | 8/1975 | Barnes, Jr. |
| 3,915,151 | A | 10/1975 | Kraus |
| RE28,907 | E | 7/1976 | Eibes et al. |

(Continued)

FOREIGN PATENT DOCUMENTS

| | | | |
|---|---|---|---|
| CN | 1697630 | A | 11/2005 |
| CN | 101040807 | A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Anu Ramana

(57) ABSTRACT

One aspect of the disclosure relates to an extramedullary biocompatible implant for moving bone in a patient's body. In some cases, the implant includes: a first plate configured to be attached to bone at a first location; a second plate configured to be attached to bone at a second location; and a distractor extending from the first plate and being at least partially contained within the second plate, where the distractor houses a drive system including a driver and a gear system coupled with the driver, and where the drive system is configured to cause translation of the second plate relative to the first plate.

17 Claims, 23 Drawing Sheets

(PC)

(56) References Cited

U.S. PATENT DOCUMENTS

| | | | |
|---|---|---|---|
| 3,976,060 A | | 8/1976 | Hildebrandt et al. |
| 4,010,758 A | | 3/1977 | Rockland et al. |
| 4,056,743 A | | 11/1977 | Clifford et al. |
| 4,068,821 A | | 1/1978 | Morrison |
| 4,078,559 A | | 3/1978 | Nissinen |
| 4,204,541 A | | 5/1980 | Kapitanov |
| 4,357,946 A | | 11/1982 | Dutcher et al. |
| 4,386,603 A | | 6/1983 | Mayfield |
| 4,448,191 A | | 5/1984 | Rodnyansky et al. |
| 4,486,176 A | | 12/1984 | Tardieu et al. |
| 4,501,266 A | | 2/1985 | McDaniel |
| 4,522,501 A | | 6/1985 | Shannon |
| 4,537,520 A | | 8/1985 | Ochiai et al. |
| 4,550,279 A | | 10/1985 | Klein |
| 4,561,798 A | | 12/1985 | Elcrin et al. |
| 4,573,454 A | | 3/1986 | Hoffman |
| 4,592,355 A | | 6/1986 | Antebi |
| 4,595,007 A | | 6/1986 | Mericle |
| 4,642,257 A | | 2/1987 | Chase |
| 4,658,809 A | | 4/1987 | Ulrich et al. |
| 4,700,091 A | | 10/1987 | Wuthrich |
| 4,747,832 A | | 5/1988 | Buffet |
| 4,854,304 A | | 8/1989 | Zielke |
| 4,904,861 A | | 2/1990 | Epstein et al. |
| 4,931,055 A | | 6/1990 | Bumpus et al. |
| 4,940,467 A | | 7/1990 | Tronzo |
| 4,957,495 A | | 9/1990 | Kluger |
| 4,973,331 A | | 11/1990 | Pursley et al. |
| 5,010,879 A | | 4/1991 | Moriya et al. |
| 5,030,235 A | | 7/1991 | Campbell, Jr. |
| 5,041,112 A | | 8/1991 | Mingozzi et al. |
| 5,064,004 A | | 11/1991 | Lundell |
| 5,074,882 A | | 12/1991 | Grammont et al. |
| 5,092,889 A | | 3/1992 | Campbell, Jr. |
| 5,133,716 A | | 7/1992 | Plaza |
| 5,142,407 A | | 8/1992 | Varaprasad et al. |
| 5,156,605 A | | 10/1992 | Pursley et al. |
| 5,263,955 A | | 11/1993 | Baumgart et al. |
| 5,290,289 A | | 3/1994 | Sanders et al. |
| 5,306,275 A | | 4/1994 | Bryan |
| 5,330,503 A | | 7/1994 | Yoon |
| 5,334,202 A | | 8/1994 | Carter |
| 5,336,223 A | | 8/1994 | Rogers |
| 5,356,411 A | | 10/1994 | Spievack |
| 5,356,424 A | | 10/1994 | Buzerak et al. |
| 5,364,396 A | | 11/1994 | Robinson et al. |
| 5,403,322 A | | 4/1995 | Herzenberg et al. |
| 5,429,638 A | | 7/1995 | Muschler et al. |
| 5,437,266 A | | 8/1995 | McPherson et al. |
| 5,466,261 A | | 11/1995 | Richelsoph |
| 5,468,030 A | | 11/1995 | Walling |
| 5,480,437 A | | 1/1996 | Draenert |
| 5,509,888 A | | 4/1996 | Miller |
| 5,516,335 A | | 5/1996 | Kummer et al. |
| 5,527,309 A | | 6/1996 | Shelton |
| 5,536,269 A | | 7/1996 | Spievack |
| 5,549,610 A | | 8/1996 | Russell et al. |
| 5,573,012 A | | 11/1996 | McEwan |
| 5,575,790 A | | 11/1996 | Chen et al. |
| 5,582,616 A | | 12/1996 | Bolduc et al. |
| 5,620,445 A | | 4/1997 | Brosnahan et al. |
| 5,620,449 A | | 4/1997 | Faccioli et al. |
| 5,626,579 A | | 5/1997 | Muschler et al. |
| 5,626,613 A | | 5/1997 | Schmieding |
| 5,632,744 A | | 5/1997 | Campbell, Jr. |
| 5,659,217 A | | 8/1997 | Petersen |
| 5,662,683 A | | 9/1997 | Kay |
| 5,672,175 A | | 9/1997 | Martin |
| 5,672,177 A | | 9/1997 | Seldin |
| 5,700,263 A | | 12/1997 | Schendel |
| 5,704,938 A | | 1/1998 | Staehlin et al. |
| 5,704,939 A | | 1/1998 | Justin |
| 5,720,746 A | | 2/1998 | Soubeiran |
| 5,743,910 A | | 4/1998 | Bays et al. |
| 5,762,599 A | | 6/1998 | Sohn |
| 5,771,903 A | | 6/1998 | Jakobsson |
| 5,810,815 A | | 9/1998 | Morales |
| 5,827,286 A | | 10/1998 | Incavo et al. |
| 5,830,221 A | | 11/1998 | Stein et al. |
| 5,879,375 A | | 3/1999 | Larson, Jr. et al. |
| 5,902,304 A | | 5/1999 | Walker et al. |
| 5,935,127 A | | 8/1999 | Border |
| 5,945,762 A | | 8/1999 | Chen et al. |
| 5,961,553 A | | 10/1999 | Coty et al. |
| 5,976,138 A | | 11/1999 | Baumgart et al. |
| 5,979,456 A | | 11/1999 | Magovern |
| 6,022,349 A | | 2/2000 | McLeod et al. |
| 6,033,412 A | | 3/2000 | Losken et al. |
| 6,034,296 A | | 3/2000 | Elvin et al. |
| 6,102,922 A | | 8/2000 | Jakobsson et al. |
| 6,106,525 A | | 8/2000 | Sachse |
| 6,113,599 A | * | 9/2000 | Landsberger ........ A61B 17/663 606/57 |
| 6,126,660 A | | 10/2000 | Dietz |
| 6,126,661 A | | 10/2000 | Faccioli et al. |
| 6,138,681 A | | 10/2000 | Chen et al. |
| 6,139,316 A | | 10/2000 | Sachdeva et al. |
| 6,162,223 A | | 12/2000 | Orsak et al. |
| 6,183,476 B1 | | 2/2001 | Gerhardt et al. |
| 6,200,317 B1 | | 3/2001 | Aalsma et al. |
| 6,234,956 B1 | | 5/2001 | He et al. |
| 6,241,730 B1 | | 6/2001 | Alby |
| 6,245,075 B1 | | 6/2001 | Betz et al. |
| 6,315,784 B1 | | 11/2001 | Djurovic |
| 6,319,255 B1 | | 11/2001 | Grundei et al. |
| 6,331,744 B1 | | 12/2001 | Chen et al. |
| 6,336,929 B1 | | 1/2002 | Justin |
| 6,343,568 B1 | | 2/2002 | McClasky |
| 6,358,283 B1 | | 3/2002 | Hogfors et al. |
| 6,375,682 B1 | | 4/2002 | Fleischmann et al. |
| 6,389,187 B1 | | 5/2002 | Greenaway et al. |
| 6,400,980 B1 | | 6/2002 | Lemelson |
| 6,402,753 B1 | | 6/2002 | Cole et al. |
| 6,409,175 B1 | | 6/2002 | Evans et al. |
| 6,416,516 B1 | | 7/2002 | Stauch et al. |
| 6,499,907 B1 | | 12/2002 | Baur |
| 6,500,110 B1 | | 12/2002 | Davey et al. |
| 6,508,820 B2 | | 1/2003 | Bales |
| 6,510,345 B1 | | 1/2003 | Van Bentem |
| 6,537,196 B1 | | 3/2003 | Creighton, IV et al. |
| 6,554,831 B1 | | 4/2003 | Rivard et al. |
| 6,565,573 B1 | | 5/2003 | Ferrante et al. |
| 6,565,576 B1 | | 5/2003 | Stauch et al. |
| 6,582,313 B2 | | 6/2003 | Perrow |
| 6,583,630 B2 | | 6/2003 | Mendes et al. |
| 6,616,669 B2 | | 9/2003 | Ogilvie et al. |
| 6,626,917 B1 | | 9/2003 | Craig |
| 6,656,135 B2 | | 12/2003 | Zogbi et al. |
| 6,656,194 B1 | | 12/2003 | Gannoe et al. |
| 6,667,725 B1 | | 12/2003 | Simons et al. |
| 6,673,079 B1 | | 1/2004 | Kane |
| 6,702,816 B2 | | 3/2004 | Buhler |
| 6,706,042 B2 | | 3/2004 | Taylor |
| 6,709,293 B2 | | 3/2004 | Mori et al. |
| 6,730,087 B1 | | 5/2004 | Butsch |
| 6,761,503 B2 | | 7/2004 | Breese |
| 6,769,499 B2 | | 8/2004 | Cargill et al. |
| 6,789,442 B2 | | 9/2004 | Forch |
| 6,796,984 B2 | | 9/2004 | Soubeiran |
| 6,802,844 B2 | | 10/2004 | Ferree |
| 6,809,434 B1 | | 10/2004 | Duncan et al. |
| 6,835,207 B2 | | 12/2004 | Zacouto et al. |
| 6,852,113 B2 | | 2/2005 | Nathanson et al. |
| 6,918,838 B2 | | 7/2005 | Schwarzler et al. |
| 6,918,910 B2 | | 7/2005 | Smith et al. |
| 6,921,400 B2 | | 7/2005 | Sohngen |
| 6,923,951 B2 | | 8/2005 | Contag et al. |
| 6,971,143 B2 | | 12/2005 | Domroese |
| 7,001,346 B2 | | 2/2006 | White |
| 7,008,425 B2 | | 3/2006 | Phillips |
| 7,011,658 B2 | | 3/2006 | Young |
| 7,029,472 B1 | | 4/2006 | Fortin |
| 7,029,475 B2 | | 4/2006 | Panjabi |
| 7,041,105 B2 | | 5/2006 | Michelson |

(56) References Cited

U.S. PATENT DOCUMENTS 7,060,080 B2 6/2006 Bachmann
7,063,706 B2 6/2006 Wittenstein
7,105,029 B2 9/2006 Doubler et al.
7,105,968 B2 9/2006 Nissen
7,114,501 B2 10/2006 Johnson et al.
7,115,129 B2 10/2006 Heggeness
7,135,022 B2 11/2006 Kosashvili et al.
7,160,312 B2 1/2007 Saadat
7,163,538 B2 1/2007 Altarac et al.
7,189,005 B2 3/2007 Ward
7,191,007 B2 3/2007 Desai et al.
7,218,232 B2 5/2007 DiSilvestro et al.
7,238,191 B2 7/2007 Bachmann
7,241,300 B2 7/2007 Sharkawy et al.
7,243,719 B2 7/2007 Baron et al.
7,255,682 B1 8/2007 Bartol, Jr. et al.
7,282,023 B2 10/2007 Frering
7,285,087 B2 10/2007 Moaddeb et al.
7,302,015 B2 11/2007 Kim et al.
7,302,858 B2 12/2007 Walsh et al.
7,314,443 B2 1/2008 Jordan et al.
7,333,013 B2 2/2008 Berger
7,357,037 B2 4/2008 Hnat et al.
7,357,635 B2 4/2008 Belfor et al.
7,360,542 B2 4/2008 Nelson et al.
7,390,007 B2 6/2008 Helms et al.
7,390,294 B2 6/2008 Hassler, Jr.
7,402,134 B2 7/2008 Moaddeb et al.
7,402,176 B2 7/2008 Malek
7,429,259 B2 9/2008 Cadeddu et al.
7,445,010 B2 11/2008 Kugler et al.
7,458,981 B2 12/2008 Fielding et al.
7,485,149 B1 2/2009 White
7,489,495 B2 2/2009 Stevenson
7,530,981 B2 5/2009 Kutsenko
7,531,002 B2 5/2009 Sutton et al.
7,553,298 B2 6/2009 Hunt et al.
7,561,916 B2 7/2009 Hunt et al.
7,611,526 B2 11/2009 Carl et al.
7,618,435 B2 11/2009 Opolski
7,658,754 B2 2/2010 Zhang et al.
7,666,184 B2 2/2010 Stauch
7,666,210 B2 2/2010 Franck et al.
7,678,136 B2 3/2010 Doubler et al.
7,678,139 B2 3/2010 Garamszegi et al.
7,708,737 B2 5/2010 Kraft et al.
7,708,762 B2 5/2010 McCarthy et al.
7,727,143 B2 6/2010 Birk et al.
7,753,913 B2 7/2010 Szakelyhidi, Jr. et al.
7,753,915 B1 7/2010 Eksler et al.
7,762,998 B2 7/2010 Birk et al.
7,763,080 B2 7/2010 Southworth
7,766,855 B2 8/2010 Miethke
7,775,215 B2 8/2010 Hassler, Jr. et al.
7,776,068 B2 8/2010 Ainsworth et al.
7,776,075 B2 8/2010 Bruneau et al.
7,787,958 B2 8/2010 Stevenson
7,794,476 B2 9/2010 Wisnewski
7,811,328 B2 10/2010 Molz, IV et al.
7,835,779 B2 11/2010 Anderson et al.
7,837,691 B2 11/2010 Cordes et al.
7,862,586 B2 1/2011 Malek
7,867,235 B2 1/2011 Fell et al.
7,875,033 B2 1/2011 Richter et al.
7,901,381 B2 3/2011 Birk et al.
7,909,852 B2 3/2011 Boomer et al.
7,918,844 B2 4/2011 Byrum et al.
7,938,841 B2 5/2011 Sharkawy et al.
7,985,256 B2 7/2011 Grotz et al.
7,988,709 B2 8/2011 Clark et al.
7,998,216 B2 * 8/2011 Elsalanty ........... A61B 17/8071
623/17.17
8,002,809 B2 8/2011 Baynham
8,011,308 B2 9/2011 Picchio
8,034,080 B2 10/2011 Malandain et al.
8,043,299 B2 10/2011 Conway
8,043,338 B2 10/2011 Dant
8,057,473 B2 11/2011 Orsak et al.
8,057,513 B2 11/2011 Kohm et al.
8,083,741 B2 12/2011 Morgan et al.
8,092,499 B1 1/2012 Roth
8,095,317 B2 1/2012 Ekseth et al.
8,105,360 B1 1/2012 Connor
8,114,158 B2 2/2012 Carl et al.
8,123,805 B2 2/2012 Makower et al.
8,133,280 B2 3/2012 Voellmicke et al.
8,147,549 B2 4/2012 Metcalf, Jr. et al.
8,162,897 B2 4/2012 Byrum
8,162,979 B2 4/2012 Sachs et al.
8,177,789 B2 5/2012 Magill et al.
8,197,490 B2 6/2012 Pool et al.
8,211,149 B2 7/2012 Justis
8,211,151 B2 7/2012 Schwab et al.
8,221,420 B2 7/2012 Keller
8,226,690 B2 7/2012 Altarac et al.
8,236,002 B2 8/2012 Fortin et al.
8,241,331 B2 8/2012 Arnin
8,246,630 B2 8/2012 Manzi et al.
8,252,063 B2 8/2012 Stauch
8,267,969 B2 9/2012 Altarac et al.
8,278,941 B2 10/2012 Kroh et al.
8,282,671 B2 10/2012 Connor
8,323,290 B2 12/2012 Metzger et al.
8,357,182 B2 1/2013 Seme
8,366,628 B2 2/2013 Denker et al.
8,372,078 B2 2/2013 Collazo
8,386,018 B2 2/2013 Stauch et al.
8,394,124 B2 3/2013 Biyani
8,403,958 B2 3/2013 Schwab
8,414,584 B2 4/2013 Brigido
8,425,608 B2 4/2013 Dewey et al.
8,435,268 B2 5/2013 Thompson et al.
8,439,926 B2 5/2013 Bojarski et al.
8,444,693 B2 5/2013 Reiley
8,469,908 B2 6/2013 Asfora
8,470,004 B2 6/2013 Reiley
8,486,070 B2 7/2013 Morgan et al.
8,486,076 B2 7/2013 Chavarria et al.
8,486,147 B2 7/2013 De Villiers et al.
8,494,805 B2 7/2013 Roche et al.
8,496,662 B2 7/2013 Novak et al.
8,518,062 B2 8/2013 Cole et al.
8,523,866 B2 9/2013 Sidebotham et al.
8,529,474 B2 9/2013 Gupta et al.
8,529,606 B2 9/2013 Alamin et al.
8,529,607 B2 9/2013 Alamin et al.
8,556,901 B2 10/2013 Anthony et al.
8,556,911 B2 10/2013 Mehta et al.
8,556,975 B2 10/2013 Ciupik et al.
8,562,653 B2 10/2013 Alamin et al.
8,568,457 B2 10/2013 Hunziker
8,579,979 B2 11/2013 Edie et al.
8,585,595 B2 11/2013 Heilman
8,585,740 B1 11/2013 Ross et al.
8,591,549 B2 11/2013 Lange
8,591,553 B2 11/2013 Eisermann et al.
8,613,758 B2 12/2013 Linares
8,617,220 B2 12/2013 Skaggs
8,623,036 B2 1/2014 Harrison et al.
8,632,544 B2 1/2014 Haaja et al.
8,632,548 B2 1/2014 Soubeiran
8,632,563 B2 1/2014 Nagase et al.
8,636,771 B2 1/2014 Butler et al.
8,636,802 B2 1/2014 Serhan et al.
8,641,719 B2 2/2014 Gephart et al.
8,641,723 B2 2/2014 Connor
8,657,856 B2 2/2014 Gephart et al.
8,663,285 B2 3/2014 Dall et al.
8,663,287 B2 3/2014 Butler et al.
8,668,719 B2 3/2014 Alamin et al.
8,709,090 B2 4/2014 Makower et al.
8,758,347 B2 6/2014 Weiner et al.
8,758,355 B2 6/2014 Fisher et al.
8,771,272 B2 7/2014 LeCronier et al.

(56) References Cited

U.S. PATENT DOCUMENTS

| | | | |
|---|---|---|---|
| 8,777,947 | B2 | 7/2014 | Zahrly et al. |
| 8,777,995 | B2 | 7/2014 | McClintock et al. |
| 8,790,343 | B2 | 7/2014 | McClellan et al. |
| 8,790,409 | B2 | 7/2014 | Van den Heuvel et al. |
| 8,828,058 | B2 | 9/2014 | Elsebaie et al. |
| 8,828,087 | B2 | 9/2014 | Stone et al. |
| 8,840,651 | B2 | 9/2014 | Reiley |
| 8,870,881 | B2 | 10/2014 | Rezach et al. |
| 8,870,959 | B2 | 10/2014 | Arnin |
| 8,915,915 | B2 | 12/2014 | Harrison et al. |
| 8,915,917 | B2 | 12/2014 | Doherty et al. |
| 8,920,422 | B2 | 12/2014 | Homeier et al. |
| 8,945,188 | B2 | 2/2015 | Rezach et al. |
| 8,961,521 | B2 | 2/2015 | Keefer et al. |
| 8,961,567 | B2 | 2/2015 | Hunziker |
| 8,968,402 | B2 | 3/2015 | Myers et al. |
| 8,992,527 | B2 | 3/2015 | Guichet |
| 9,022,917 | B2 | 5/2015 | Kasic et al. |
| 9,044,218 | B2 | 6/2015 | Young |
| 9,060,810 | B2 | 6/2015 | Kercher et al. |
| 9,078,703 | B2 | 7/2015 | Arnin |
| 9,179,938 | B2 | 11/2015 | Pool et al. |
| 10,736,664 | B2 * | 8/2020 | Strozyk ................ A61B 17/663 |
| 2002/0050112 | A1 | 5/2002 | Koch et al. |
| 2002/0072758 | A1 | 6/2002 | Reo et al. |
| 2002/0164905 | A1 | 11/2002 | Bryant |
| 2003/0040671 | A1 | 2/2003 | Somogyi et al. |
| 2003/0144669 | A1 | 7/2003 | Robinson |
| 2003/0220643 | A1 | 11/2003 | Ferree |
| 2003/0220644 | A1 | 11/2003 | Thelen et al. |
| 2004/0011137 | A1 | 1/2004 | Hnat et al. |
| 2004/0011365 | A1 | 1/2004 | Govari et al. |
| 2004/0019353 | A1 | 1/2004 | Freid et al. |
| 2004/0023623 | A1 | 2/2004 | Stauch et al. |
| 2004/0055610 | A1 | 3/2004 | Forsell |
| 2004/0133219 | A1 | 7/2004 | Forsell |
| 2004/0138725 | A1 | 7/2004 | Forsell |
| 2004/0193266 | A1 | 9/2004 | Meyer |
| 2005/0034705 | A1 | 2/2005 | McClendon |
| 2005/0049617 | A1 | 3/2005 | Chatlynne et al. |
| 2005/0065529 | A1 | 3/2005 | Liu et al. |
| 2005/0090823 | A1 | 4/2005 | Bartimus |
| 2005/0159754 | A1 | 7/2005 | Odrich |
| 2005/0234448 | A1 | 10/2005 | McCarthy |
| 2005/0234462 | A1 | 10/2005 | Hershberger |
| 2005/0246034 | A1 | 11/2005 | Soubeiran |
| 2005/0261779 | A1 | 11/2005 | Meyer |
| 2005/0272976 | A1 | 12/2005 | Tanaka et al. |
| 2006/0004459 | A1 | 1/2006 | Hazebrouck et al. |
| 2006/0009767 | A1 | 1/2006 | Kiester |
| 2006/0036259 | A1 | 2/2006 | Carl et al. |
| 2006/0036323 | A1 | 2/2006 | Carl et al. |
| 2006/0036324 | A1 | 2/2006 | Sachs et al. |
| 2006/0047282 | A1 | 3/2006 | Gordon |
| 2006/0058792 | A1 | 3/2006 | Hynes |
| 2006/0069447 | A1 | 3/2006 | DiSilvestro et al. |
| 2006/0074448 | A1 | 4/2006 | Harrison et al. |
| 2006/0079897 | A1 | 4/2006 | Harrison et al. |
| 2006/0136062 | A1 | 6/2006 | DiNello et al. |
| 2006/0142767 | A1 | 6/2006 | Green et al. |
| 2006/0155279 | A1 | 7/2006 | Ogilvie |
| 2006/0195087 | A1 | 8/2006 | Sacher et al. |
| 2006/0195088 | A1 | 8/2006 | Sacher et al. |
| 2006/0200134 | A1 | 9/2006 | Freid et al. |
| 2006/0204156 | A1 | 9/2006 | Takehara et al. |
| 2006/0235299 | A1 | 10/2006 | Martinelli |
| 2006/0235424 | A1 | 10/2006 | Vitale et al. |
| 2006/0241746 | A1 | 10/2006 | Shaoulian et al. |
| 2006/0241767 | A1 | 10/2006 | Doty |
| 2006/0249914 | A1 | 11/2006 | Dulin |
| 2006/0271107 | A1 | 11/2006 | Harrison et al. |
| 2006/0282073 | A1 | 12/2006 | Simanovsky |
| 2006/0293683 | A1 | 12/2006 | Stauch |
| 2007/0010814 | A1 | 1/2007 | Stauch |
| 2007/0010887 | A1 | 1/2007 | Williams et al. |
| 2007/0021644 | A1 | 1/2007 | Woolson et al. |
| 2007/0031131 | A1 | 2/2007 | Griffitts |
| 2007/0043376 | A1 | 2/2007 | Leatherbury et al. |
| 2007/0050030 | A1 | 3/2007 | Kim |
| 2007/0118215 | A1 | 5/2007 | Moaddeb |
| 2007/0161984 | A1 | 7/2007 | Cresina et al. |
| 2007/0173837 | A1 | 7/2007 | Chan et al. |
| 2007/0179493 | A1 | 8/2007 | Kim |
| 2007/0185374 | A1 | 8/2007 | Kick et al. |
| 2007/0233098 | A1 | 10/2007 | Mastrorio et al. |
| 2007/0239159 | A1 | 10/2007 | Altarac et al. |
| 2007/0239161 | A1 | 10/2007 | Giger et al. |
| 2007/0255088 | A1 | 11/2007 | Jacobson et al. |
| 2007/0270803 | A1 | 11/2007 | Giger et al. |
| 2007/0276368 | A1 | 11/2007 | Trieu et al. |
| 2007/0276369 | A1 | 11/2007 | Allard et al. |
| 2007/0276373 | A1 | 11/2007 | Malandain |
| 2007/0276378 | A1 | 11/2007 | Harrison et al. |
| 2007/0276493 | A1 | 11/2007 | Malandain et al. |
| 2007/0288024 | A1 | 12/2007 | Gollogly |
| 2007/0288183 | A1 | 12/2007 | Bulkes et al. |
| 2008/0009792 | A1 | 1/2008 | Henniges et al. |
| 2008/0015577 | A1 | 1/2008 | Loeb |
| 2008/0021454 | A1 | 1/2008 | Chao et al. |
| 2008/0021455 | A1 | 1/2008 | Chao et al. |
| 2008/0021456 | A1 | 1/2008 | Gupta et al. |
| 2008/0027436 | A1 | 1/2008 | Cournoyer et al. |
| 2008/0033431 | A1 | 2/2008 | Jung et al. |
| 2008/0033436 | A1 | 2/2008 | Song et al. |
| 2008/0051784 | A1 | 2/2008 | Gollogly |
| 2008/0082118 | A1 | 4/2008 | Edidin et al. |
| 2008/0086128 | A1 | 4/2008 | Lewis |
| 2008/0097487 | A1 | 4/2008 | Pool et al. |
| 2008/0097496 | A1 | 4/2008 | Chang et al. |
| 2008/0108995 | A1 | 5/2008 | Conway et al. |
| 2008/0161933 | A1 | 7/2008 | Grotz et al. |
| 2008/0167685 | A1 | 7/2008 | Allard et al. |
| 2008/0172063 | A1 | 7/2008 | Taylor |
| 2008/0177319 | A1 | 7/2008 | Schwab |
| 2008/0177326 | A1 | 7/2008 | Thompson |
| 2008/0190237 | A1 | 8/2008 | Radinger et al. |
| 2008/0228186 | A1 | 9/2008 | Gall et al. |
| 2008/0255615 | A1 | 10/2008 | Vittur et al. |
| 2008/0272928 | A1 | 11/2008 | Shuster |
| 2008/0275557 | A1 | 11/2008 | Makower et al. |
| 2009/0030462 | A1 | 1/2009 | Buttermann |
| 2009/0076597 | A1 | 3/2009 | Dahlgren et al. |
| 2009/0082815 | A1 | 3/2009 | Zylber et al. |
| 2009/0088803 | A1 | 4/2009 | Justis et al. |
| 2009/0093820 | A1 | 4/2009 | Trieu et al. |
| 2009/0093890 | A1 | 4/2009 | Gelbart |
| 2009/0112263 | A1 | 4/2009 | Pool et al. |
| 2009/0163780 | A1 | 6/2009 | Tieu |
| 2009/0171356 | A1 | 7/2009 | Klett |
| 2009/0192514 | A1 | 7/2009 | Feinberg et al. |
| 2009/0198144 | A1 | 8/2009 | Phillips et al. |
| 2009/0216113 | A1 | 8/2009 | Meier et al. |
| 2009/0275984 | A1 | 11/2009 | Kim et al. |
| 2010/0004654 | A1 | 1/2010 | Schmitz et al. |
| 2010/0057127 | A1 | 3/2010 | McGuire et al. |
| 2010/0094306 | A1 | 4/2010 | Chang et al. |
| 2010/0100185 | A1 | 4/2010 | Trieu et al. |
| 2010/0106192 | A1 | 4/2010 | Barry |
| 2010/0114322 | A1 | 5/2010 | Clifford et al. |
| 2010/0130941 | A1 | 5/2010 | Conlon et al. |
| 2010/0137872 | A1 | 6/2010 | Kam et al. |
| 2010/0145449 | A1 | 6/2010 | Makower et al. |
| 2010/0145462 | A1 | 6/2010 | Ainsworth et al. |
| 2010/0168751 | A1 | 7/2010 | Anderson et al. |
| 2010/0249782 | A1 | 9/2010 | Durham |
| 2010/0256626 | A1 | 10/2010 | Muller et al. |
| 2010/0262239 | A1 | 10/2010 | Boyden et al. |
| 2010/0318129 | A1 | 12/2010 | Seme et al. |
| 2010/0331883 | A1 | 12/2010 | Schmitz et al. |
| 2011/0004076 | A1 | 1/2011 | Janna et al. |
| 2011/0057756 | A1 | 3/2011 | Marinescu et al. |
| 2011/0066188 | A1 | 3/2011 | Seme et al. |
| 2011/0098748 | A1 | 4/2011 | Jangra |
| 2011/0152725 | A1 | 6/2011 | Demir et al. |

(56) References Cited

U.S. PATENT DOCUMENTS

| | | | | |
|---|---|---|---|---|
| 2011/0196435 | A1 | 8/2011 | Forsell | |
| 2011/0202138 | A1 | 8/2011 | Shenoy et al. | |
| 2011/0238126 | A1 | 9/2011 | Soubeiran | |
| 2011/0257655 | A1 | 10/2011 | Copf, Jr. | |
| 2011/0284014 | A1 | 11/2011 | Cadeddu et al. | |
| 2012/0019341 | A1 | 1/2012 | Gabay et al. | |
| 2012/0019342 | A1 | 1/2012 | Gabay et al. | |
| 2012/0053633 | A1 | 3/2012 | Stauch | |
| 2012/0088953 | A1 | 4/2012 | King | |
| 2012/0109207 | A1 | 5/2012 | Trieu | |
| 2012/0116535 | A1 | 5/2012 | Ratron et al. | |
| 2012/0158061 | A1 | 6/2012 | Koch et al. | |
| 2012/0172883 | A1 | 7/2012 | Sayago | |
| 2012/0179215 | A1 | 7/2012 | Soubeiran | |
| 2012/0221106 | A1 | 8/2012 | Makower et al. | |
| 2012/0271353 | A1 | 10/2012 | Barry | |
| 2012/0296234 | A1 | 11/2012 | Wilhelm et al. | |
| 2012/0329882 | A1 | 12/2012 | Messersmith et al. | |
| 2013/0013066 | A1 | 1/2013 | Landry et al. | |
| 2013/0072932 | A1 | 3/2013 | Stauch | |
| 2013/0123847 | A1 | 5/2013 | Anderson et al. | |
| 2013/0138017 | A1 | 5/2013 | Jundt et al. | |
| 2013/0138154 | A1 | 5/2013 | Reiley | |
| 2013/0150863 | A1 | 6/2013 | Baumgartner | |
| 2013/0150889 | A1 | 6/2013 | Fening et al. | |
| 2013/0178903 | A1 | 7/2013 | Abdou | |
| 2013/0211521 | A1 | 8/2013 | Shenoy et al. | |
| 2013/0245692 | A1 | 9/2013 | Hayes et al. | |
| 2013/0253344 | A1 | 9/2013 | Griswold et al. | |
| 2013/0253587 | A1 | 9/2013 | Carls et al. | |
| 2013/0261672 | A1 | 10/2013 | Horvath | |
| 2013/0296863 | A1 | 11/2013 | Globerman et al. | |
| 2013/0296864 | A1 | 11/2013 | Burley et al. | |
| 2013/0296940 | A1 | 11/2013 | Northcutt et al. | |
| 2013/0325006 | A1 | 12/2013 | Michelinie et al. | |
| 2013/0325071 | A1 | 12/2013 | Niemiec et al. | |
| 2014/0005788 | A1 | 1/2014 | Haaja et al. | |
| 2014/0025172 | A1 | 1/2014 | Lucas et al. | |
| 2014/0052134 | A1 | 2/2014 | Orisek | |
| 2014/0058392 | A1 | 2/2014 | Mueckter et al. | |
| 2014/0058450 | A1 | 2/2014 | Arlet | |
| 2014/0066987 | A1 | 3/2014 | Hestad et al. | |
| 2014/0088715 | A1 | 3/2014 | Ciupik | |
| 2014/0128920 | A1 | 5/2014 | Kantelhardt | |
| 2014/0155946 | A1 | 6/2014 | Skinlo et al. | |
| 2014/0163664 | A1 | 6/2014 | Goldsmith | |
| 2014/0236234 | A1 | 8/2014 | Kroll et al. | |
| 2014/0236311 | A1 | 8/2014 | Vicatos et al. | |
| 2014/0257412 | A1 | 9/2014 | Patty et al. | |
| 2014/0277446 | A1 | 9/2014 | Clifford et al. | |
| 2014/0296918 | A1 | 10/2014 | Fening et al. | |
| 2014/0303538 | A1 | 10/2014 | Baym et al. | |
| 2014/0303539 | A1 | 10/2014 | Baym et al. | |
| 2014/0358150 | A1 | 12/2014 | Kaufman et al. | |
| 2015/0105782 | A1 | 4/2015 | D'Lima et al. | |
| 2015/0105824 | A1 | 4/2015 | Moskowitz et al. | |
| 2015/0272644 | A1 | 10/2015 | Noon et al. | |
| 2022/0387086 | A1 * | 12/2022 | Penn, IV | A61B 17/8071 |

FOREIGN PATENT DOCUMENTS

| | | | | |
|---|---|---|---|---|
| DE | 1541262 | A1 | 6/1969 | |
| DE | 8515687 | U1 | 12/1985 | |
| DE | 19626230 | A1 | 1/1998 | |
| DE | 19745654 | A1 | 4/1999 | |
| DE | 102005045070 | A1 | 4/2007 | |
| EP | 0663184 | A1 | 7/1995 | |
| EP | 1905388 | A1 | 4/2008 | |
| EP | 3125792 | B1 * | 1/2019 | A61B 17/8071 |
| FR | 2901991 | A1 | 12/2007 | |
| FR | 2900563 | B1 | 8/2008 | |
| FR | 2892617 | B1 | 9/2008 | |
| FR | 2916622 | B1 | 9/2009 | |
| FR | 2961386 | B1 | 12/2011 | |
| JP | H0956736 | | 3/1997 | |
| JP | 2002500063 | A | 1/2002 | |
| WO | WO1998044858 | A1 | 10/1998 | |
| WO | WO1999051160 | A1 | 10/1999 | |
| WO | WO2001024697 | A1 | 4/2001 | |
| WO | WO2001045485 | A3 | 6/2001 | |
| WO | WO2001045487 | A2 | 6/2001 | |
| WO | WO2001067973 | A2 | 9/2001 | |
| WO | WO2001078614 | A1 | 10/2001 | |
| WO | WO2007013059 | A3 | 2/2007 | |
| WO | WO2007015239 | A3 | 2/2007 | |
| WO | WO2011116158 | A3 | 9/2011 | |
| WO | WO2013119528 | A1 | 8/2013 | |
| WO | WO2014040013 | A1 | 3/2014 | |
| WO | 2020/069627 | A1 | 4/2020 | |
| WO | 2022/015898 | A1 | 1/2022 | |

OTHER PUBLICATIONS

Ahlbom et al., "Guidelines for limiting exposure to time-varying electric, magnetic, and electromagnetic fields (up to 300 GHZ). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

(56) References Cited

OTHER PUBLICATIONS

Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.

(56) References Cited

OTHER PUBLICATIONS

Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

* cited by examiner (PC)

166
190
192
221
184
180
164
182
240
154
156
152
152
150
240
210
151
150
214A
252
254
250
728
726
746
738
214A
226
236
228
220
742
732
726
734
726
728
204
718
724
228
207
202
209
106
213
219
244
248
228
226
214C
236
246

120
312
314
104
109A
104
104
106
108
104
102
103
104
104
104
107
310
(PC)

120
104
104
109B
104
108
106
104
104
104
103
320
102

120
334
108
332
102
330

214A
219
218
219
108
104
104
104
220
214A
106
108
218
224
218A
221
214A
218
221
119
230
234
104
102
199
232

100
104
104
104
602
104
104
104
3902
3802
604
3800
104
104
104

100
104
104
602
104
104
104
104
604
3902
3802
104
3800
104

100
604
4412
4412
4414
3902
604
100
4414
4406
604
104
3902
4414
4408
4406
4412
4400
4402
100
104
104
3800
104
104
4406
4402
4404
3800
104
100

EXTRAMEDULLARY DEVICE

TECHNICAL FIELD

The subject matter described herein relates to an extramedullary distraction and compression device, systems and associated methods.

BACKGROUND

Distraction osteogenesis is a technique which has been used to grow new bone in patients with a variety of defects. For example, limb lengthening is a technique in which the length of a bone (for example a femur or tibia) may be increased. By creating a corticotomy, or osteotomy, in the bone, which is a cut through the bone, the two resulting sections of bone may be moved apart at a particular rate, such as one (1.0) mm per day, allowing new bone to regenerate between the two sections as they move apart. This technique of limb lengthening is used in cases where one limb is longer than the other, such as in a patient whose prior bone break did not heal correctly, or in a patient whose growth plate was diseased or damaged prior to maturity. In some patients, stature lengthening is desired, and is achieved by lengthening both femurs and/or both tibia to increase the patient's height.

Limb lengthening is often performed using external fixation, wherein an external distraction frame is attached to the two sections of bone by pins which pass through the skin. The pins can be sites for infection and are often painful for the patient, as the pin placement site remains a somewhat open wound "pin tract" throughout the treatment process. The external fixation frames are also bulky, making it difficult for patient to comfortably sit, sleep and move. Intramedullary lengthening devices also exist, such as those described in U.S. Patent Application Publication No. 2011/0060336, which is incorporated by reference herein.

SUMMARY

A first aspect of the disclosure relates to a biocompatible implant for moving bone in a patient's body, the implant including: a first plate configured to be attached to bone at a first location; a second plate configured to be attached to bone at a second location; and a distractor extending from the first plate and being at least partially contained within the second plate, the distractor houses a drive system including a driver and a gear system coupled with the driver, and the drive system is configured to cause translation of the second plate relative to the first plate.

A second aspect of the disclosure relates to a biocompatible implant for moving bone in a patient's body, the implant including: a first portion configured to be attached to a bone at a first location; a second portion configured to be attached to the bone at a second location; and an internal distraction component extending from the first portion and at least partially contained within the second portion, the internal distraction component housing a drive system configured to cause translation of the second portion relative to the first portion, an entirety of the drive system is contained within the internal distraction component.

Implementations may include one of the following features, or any combination thereof.

In various implementations, bone refers to at least a portion of a bone, and in particular cases, to pieces of a bone, for example, a monolithic bone that has been broken into pieces.

In certain cases, the driver is located axially between the gear system and the first plate.

In some aspects, the driver is located between a proximal end of the implant and the gear system, and a distal end of the distractor includes an output driver for mating with an input driver on the second plate. In certain cases, the output driver includes a first threaded coupler and the input driver includes a second, complementary threaded coupler.

In particular implementations, actuation of the driver engages the gear system and initiates rotation of the output driver.

In certain cases, the implant further includes at least one anti-rotation feature at an interface between the distractor and the second plate.

In some aspects, during actuation of the driver, the anti-rotation feature resists rotation of the second plate, causing translation of the second plate.

In particular implementations, the at least one anti-rotation feature includes one or more anti-rotation pegs extending radially from the distractor and one or more corresponding grooves in the second plate.

In certain cases, the one or more anti-rotation pegs extends along only a portion of an axial length of the distractor.

In particular aspects, the one or more anti-rotation pegs includes a notch at each axial end thereof.

In some implementations, the at least one anti-rotation feature includes a set of grooves on the second plate configured to resist rotation of a first set of grooves on the distractor.

In certain cases, the at least one anti-rotation feature includes one or more straight regions at the interface between the second plate and the distractor.

In some aspects, the implant further includes an end cap on a proximal end of the distractor for limiting an extent of translation of the second plate relative to the first plate.

In particular cases, the implant further includes a retaining ring extending at least partially circumferentially about the distractor, the retaining ring is located axially between the end cap and the first plate.

In some implementations, an entirety of the drive system is contained within the distractor.

In some aspects, the distractor has an outer dimension with a non-circular cross-section and the second plate has an inner dimension with a non-circular cross-section.

In certain cases, the non-circular cross-section of the outer dimension of the distractor and the non-circular cross-section of the inner dimension of the second plate cooperate to limit rotation of the second plate during actuation of the drive system.

In particular aspects, the implant further includes an anti jam feature internal to the second plate.

In some cases, the implant further includes a brake located axially between the driver and the gear system.

In certain implementations, the first plate includes a first housing substantially containing the distractor and a first connecting plate extending from the first housing, the first connecting plate including a first set of one or more holes for receiving a bone anchor, and the second plate includes a second housing including a sleeve and a second connecting plate extending from the sleeve, the second connecting plate including a second set of one or more holes for receiving a bone anchor.

In particular cases, the sleeve is sized to axially overlap the distractor.

In some aspects, the implant is movable between a fully compact position and a fully extended position, and a difference in length between the fully extended position and the fully compact position is approximately 45 millimeters (mm) to approximately 55 mm.

In certain implementations, the difference between the fully extended position and the fully compact position is at least 50 mm.

In some cases, an axial length of the implant in the fully compact position is approximately 75 mm to approximately 83 mm. In more particular aspects, the axial length of the implant in the fully compact position is approximately 78-79 mm.

In certain aspects, an axial length of the implant in the fully extended position is approximately 125 mm to approximately 133 mm. In more particular aspects, the axial length of the implant in the fully extended position is approximately 128-129 mm.

In some implementations, the driver includes a magnetic driver configured to be actuated by a controller external to the patient's body.

In particular aspects, the driver includes at least one of: an electric driver configured to be driven by an actuator in an external control device from a location external to the patient's body, or an ultrasound powered driver configured to be driven by an actuator in an external control device from a location external to the patient's body.

In some cases, the first portion of the implant includes a first plate.

In some cases, the implant is configured for extramedullary placement in a patient.

In certain implementations, the implant is configured to aid in treatment of a limb length discrepancy or a bone defect in the patient's body.

In some cases, a method of performing a trifocal transport procedure uses the biocompatible implant.

In certain aspects, a method of moving at least a portion of one of a tibia or a femur of the patient uses the biocompatible implant.

In some implementations, the drive system includes a driver and a gear system coupled with the driver.

In particular cases, the driver is located axially between the gear system and the first portion.

In certain aspects, the driver is located between a proximal end of the implant and the gear system, and a distal end of the internal distraction component includes a first threaded coupler for mating with a second threaded coupler on the second portion.

In some cases, actuation of the driver engages the gear system and initiates rotation of the first threaded coupler.

In particular implementations, a majority of an axial extent of the first plate overlaps an axial extent of the distractor, and a portion of the first plate overlaps with the distractor when both the portion of the first plate and a portion of the distractor intersect a plane perpendicular to the length of the distractor. The axial extent can refer to axial length, or length along the primary axis of distraction.

Two or more features described in this disclosure, including those described in this summary section, may be combined to form implementations not specifically described herein.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

The details of one or more implementations are set forth in the accompanying drawings and the description below. Other features, objects and benefits will be apparent from the description and drawings, and from the claims.

BRIEF DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

Figure 1:
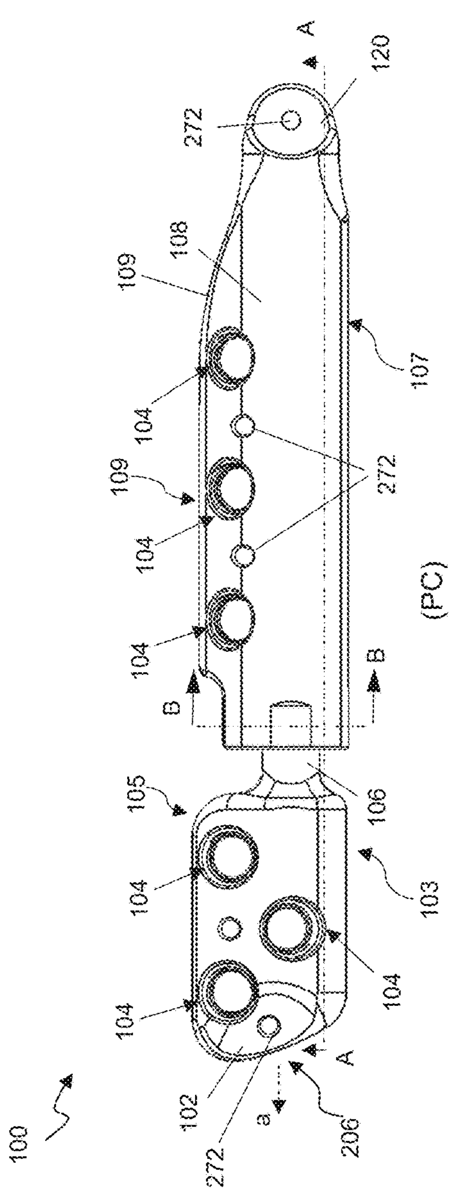
FIG. 1 shows a top-down view of an extramedullary distraction and compression device according to embodiments of the disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The present disclosure describes various embodiments of an extramedullary device, for example, a biocompatible implant for moving bone in a patient's body. Various embodiments include related bone adjustment devices, systems and associated methods. The devices, systems and methods described herein can be used for, among other things, open and closed fracture fixation, pseudoarthrosis, mal-unions and non-unions of long bones. The present disclosure includes an implant with a distractor housing a drive system for translating a set of plates. With the drive system housed in the distractor, the implant can be sized to accommodate adjustment of relatively smaller (length) bones. Because the system is extramedullary, the system also provides a solution for patients with inadequate canal space to accommodate an intramedullary lengthening device.

As will be described herein, implants disclosed according to various implementations can be configured to aid in treatment of a limb length discrepancy or a bone defect in the patient's body. Over the treatment period for limb lengthening, the bone is regularly distracted, creating a new separation, into which osteogenesis can occur. "Regularly distracted" is meant to indicate that distraction occurs on a regular or periodic basis which may be on the order of every day or every few days. An example distraction rate is one millimeter per day, although, other distraction rates may be employed. A distraction regimen can include a daily increase of about one millimeter in the length of implants disclosed herein according to various implementations. This may be done, for example, by four lengthening periods per day, each having 0.25 mm of lengthening. Other distraction or contraction regimens may be used. As noted herein, "a bone" or "bone" can refer to a single, monolithic segment (or, section) of bone, or to multiple (e.g., two) bone segments that were previously monolithic. In order to grow or lengthen bone, the bone either has a pre-existing separation or is purposely cut or broken (e.g., via an osteotomy) to create a separation, dividing the bone into a first section and a second section. The cut may be done before or after implantation of the implants disclosed herein, for example by use of a flexible Gigli saw. In some cases, a method of performing a trifocal transport procedure uses the biocompatible implant(s) disclosed according to various implementations herein. In additional cases, a method of moving at least a portion of one of a tibia or a femur of the patient uses the biocompatible implant(s) disclosed according to various implementations herein.

Figure 2:
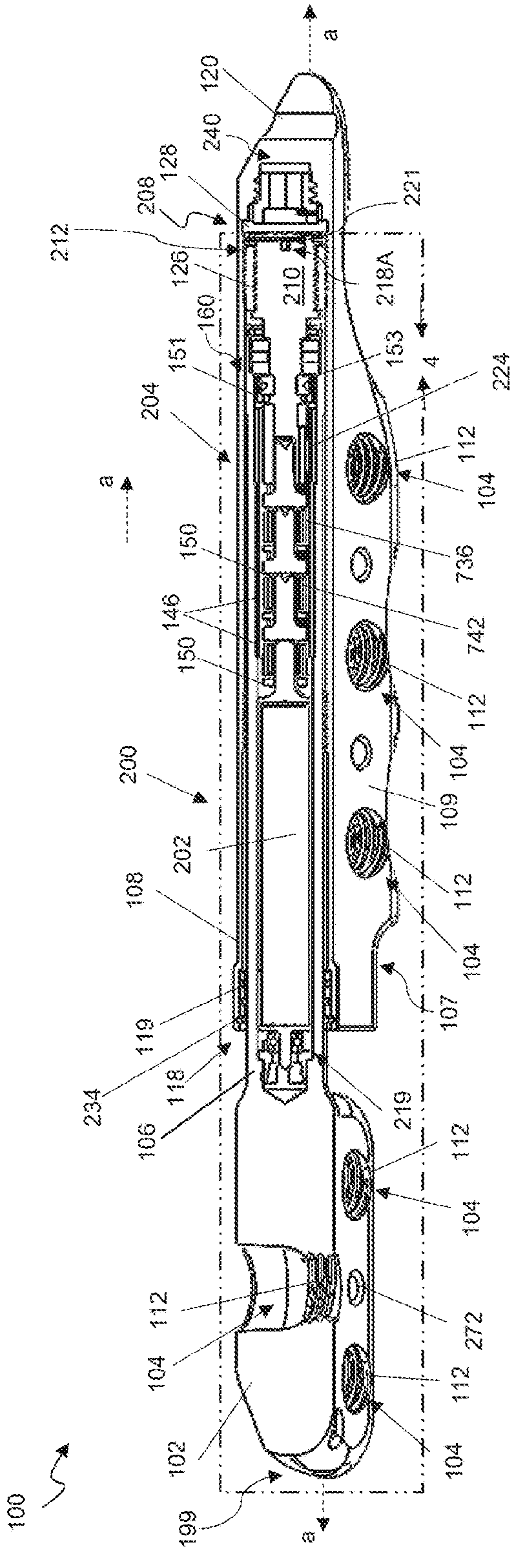
FIG. 2 shows a cross-sectional side view of the extramedullary distraction and compression device taken along line A-A of FIG. 1.

FIG. 1 shows a top-down view of a biocompatible implant (also referred to as an extramedullary distraction and compression device) 100 according to embodiments of the disclosure and FIG. 2 shows a cross-sectional view of the implant 100 taken along line A-A. As shown in FIGS. 1 and 2, the implant 100 may include a first plate 102 configured to be coupled to a bone at a first location, and a second plate 108 configured to be coupled to the bone at a second location. The implant 100 can further include a distractor 106 (e.g., a distraction and compression rod) extending from the first plate 102 and being at least partially contained within the second plate 108. As will be described herein, the distractor 106 is configured to retract (e.g., for compression) and/or distract (e.g., for limb lengthening) relative to the second plate 108 containing the distractor 106 therein. The implant 100 may be configured to allow controlled, precise translation of the first plate 102 relative to the second plate 108 by non-invasive remote control, and thus controlled, precise translation of a first bone segment secured to the first plate 102 relative to a second bone segment secured to the second plate 108.

In some cases, the first plate 102 includes a first housing 103 and a first connecting plate 105 extending from the first housing 103. In various implementations, the first housing 103 and first connecting plate 105 are formed of a continuous piece of material, e.g., a biocompatible material such as titanium. In some implementations, an outer dimension (e.g., thickness) of the first housing 103 and the first connecting plate 105 are distinct. The first connecting plate 105 can include at least one hole (or, fixation aperture) 104 for receiving a bone anchor (FIGS. 19 and 20).

Figure 19:
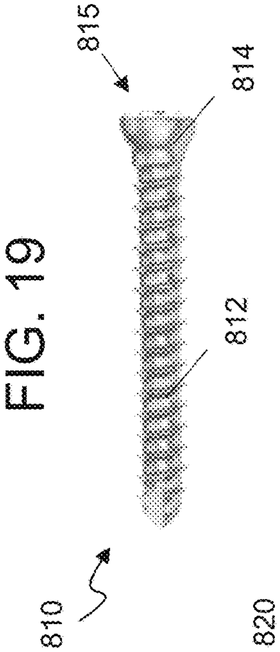
FIG. 19 shows a side view of a bi-cortical non-locking screw according to embodiments of the disclosure.
Figure 20:
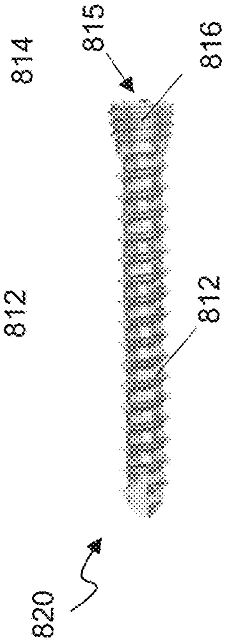
FIG. 20 shows a side view of a bi-cortical locking screw according to embodiments of the disclosure.

In some cases, the second plate 108 includes a sleeve 107 and a second connecting plate 109 extending from the sleeve 107, the second connecting plate 109 including an additional set of holes (or, fixation apertures) 104 for receiving a bone anchor (see FIGS. 19 and 20). In various implementations, the sleeve 107 and second connecting plate 109 are formed of a continuous piece of material. In some implementations, an outer dimension (e.g., thickness) of the sleeve 107 and the second connecting plate 109 are distinct. In particular cases, the sleeve 107 is sized to axially overlap the distractor 106. As shown in FIG. 2, in some embodiments the second plate 108 include an end having an opening 118 for receiving the distractor 106. One or more o-ring(s) 119 can be positioned about the distractor 106 between distractor 106 and the second plate 108. In some embodiments, a portion of the outer surface of the distractor 106 and/or a portion of an internal surface of the second plate 108 can be recessed to accommodate the o-ring(s) 119. The o-ring(s) 119 can help facilitate proper sealing between the second plate 108 and the distractor 106 so that bodily fluid does not enter the second plate 108 when the implant 100 is implanted. The second plate 108 may be sealed at the other end by the attachment of an end cap 120. The end cap 120 may be attached to the second plate 108 by means of welding, adhesive bonding, or other joining techniques. Further, an o-ring(s) 119 may be provided between the end cap 120 and the second plate 108 to help provide a seal.

In various implementations, one or both plate(s) 102, 108 can be curved or angled in a number of different configurations dependent upon where on the bone and which bone the implant 100 is to be affixed to such that the plate 102, 108 may be contoured to a shape of the bone. Further, fixation apertures 104 may be positioned about connecting plate (or bulge portion) 109 of the second plate 108. As best seen in FIG. 2, at least one fixation aperture 104 can be a locking screw hole having internal threads 112 for threadingly engaging with a thread on a head of a fixation screw as will be described herein. In some embodiments, all fixation apertures 104 have internal threads 112.

In some embodiments, as illustrated in FIGS. 1 and 2, the implant 100 includes a drive system 200 disposed within the distractor 106. The drive system 200 may be configured to increase a distance between the plates 102, 108 (e.g., displace the second plate 108 relative to the first plate 102), thus forcing a first bone section and a second bone section of apart from one another (i.e., distraction). The drive system 200 may be configured to cause translation (i.e., axial translation along an axis (a)) of the second plate 108 relative to the first plate 102. In particular cases, the distractor 106 houses a drive system 200 including a driver 202 and a gear system 204 coupled with the driver 202. As noted herein, in various implementations, an entirety of the drive system 200 is contained within the distractor 106. The driver 202 may include a magnetic driver (e.g., a rotatable permanent magnet) configured to be rotated by an externally applied magnetic field. A controller (e.g., an external adjustment device 400 of FIG. 21) including an external magnet 414, 416 (FIG. 21) may be configured to actuate rotation of the driver 202 in either of a first direction or a second direction about a rotational axis of the driver 202. During actuation of driver 202, the controller may be positioned external to the patient's body and configured to transcutaneously actuate the driver 202. In addition, or instead, implementations of the driver 202 includes one or more of: an electric driver configured to be powered by a power storage unit (e.g., a battery, capacitor, or other storage unit) of the implant 100 and charged by an external adjustment device from a location external to the patient's body. In some examples, power is not stored long term (e.g., stored for use during a later distraction session than a session in which the implant receives power) by a power storage unit. In further examples, the implant receives power ultrasonically from an ultrasound actuator in an external control device from a location external to the patient's body. As further shown in FIG. 2, the driver 202 may be located axially between the gear system 204 and the first plate 102 along the primary axis (a) of the implant 100. The illustrated driver 202 is located between a proximal end 199 of the implant 100 and the gear system 204. In particular cases, a distal end 208 of the distractor 106 includes an output driver 210 for mating with an input driver 212 on the second plate 108. According to various implementations, as noted herein, actuation of the driver 202 engages the gear system 204 and initiates rotation of the output driver 210. In certain aspects, the output driver 210 (of the distractor 106) and the input driver 212 (of the second plate 108) include threaded couplers, such as complementary threaded couplings.

Figure 11:
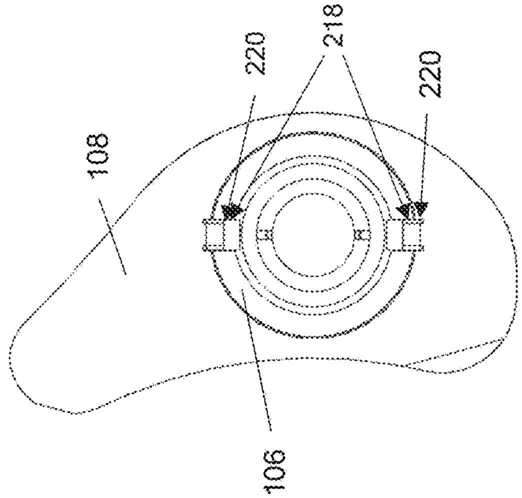
FIG. 11 shows a cross-sectional view taken along line B-B of FIG. 1 showing the anti-rotation feature.

The implant 100 can further include an anti-rotation feature 214 at an interface 216 (FIGS. 7, 10, 11) between the distractor 106 and the second plate 108, e.g., to aid in converting rotational motion from the output driver 210 to translational motion of the second plate 108. In use, actuation of the driver 202 engages the gear system 204 and initiates rotation of the output driver 210. In particular cases, during actuation of the driver 202, the output driver 210 is driven to rotate (about primary axis (a)), while the anti-rotation feature 214 resists rotation of the second plate 108, causing the second plate 108 to axially translate along primary axis (a).

Figure 3:
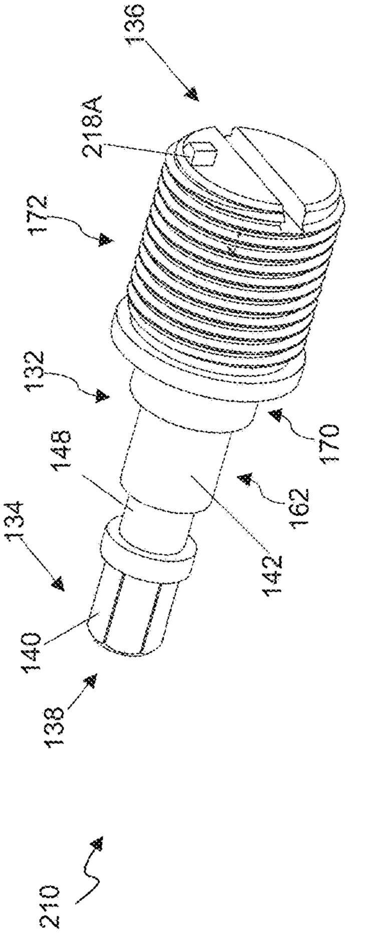
FIG. 3 shows a side view of a lead screw according to embodiments of the disclosure.
Figure 10:
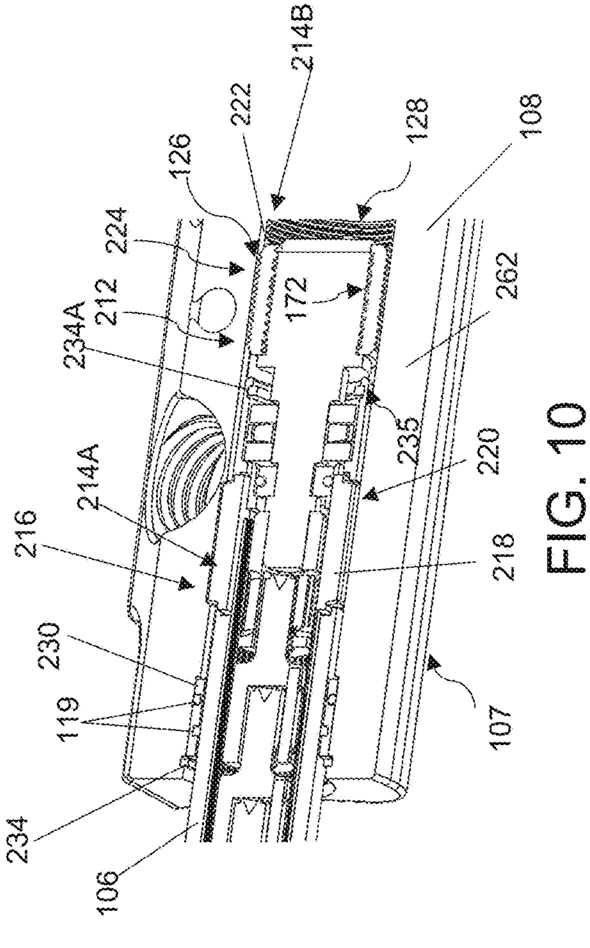
FIG. 10 shows an enlarged top-down view of an anti-rotation feature about the rod with the housing removed according to embodiments of the disclosure.
Figure 26:
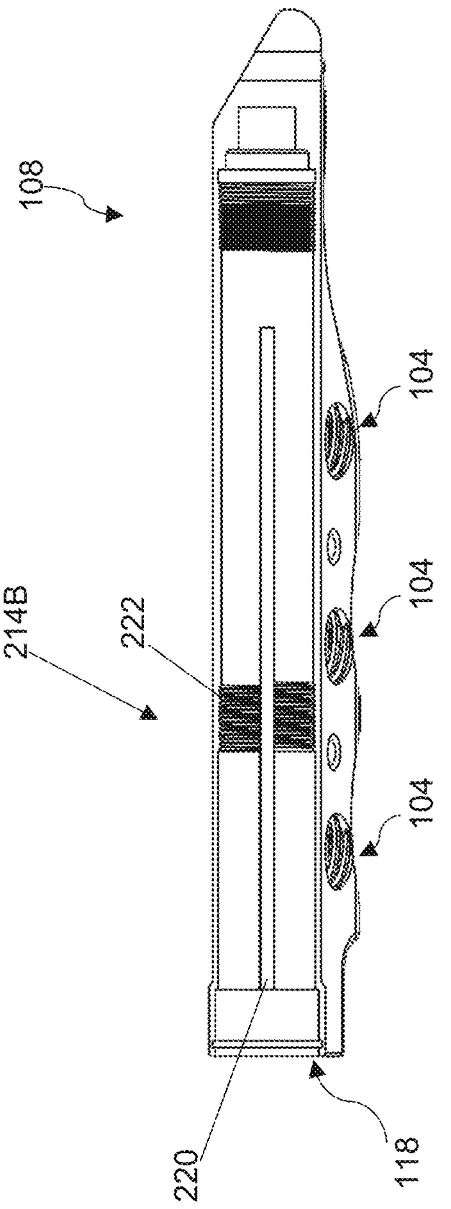
FIG. 26 a cross-sectional perspective view of the housing according to an embodiment of the disclosure.
Figure 25:
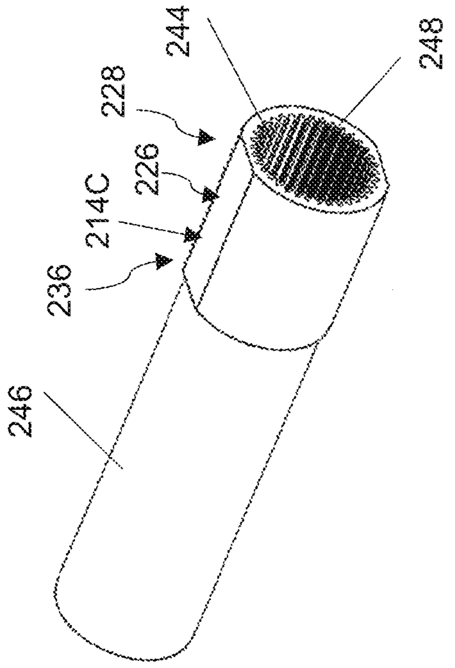
FIG. 25 shows an enlarged perspective view of an alternative embodiment of a ring gear according to embodiments of the disclosure.
Figure 28:
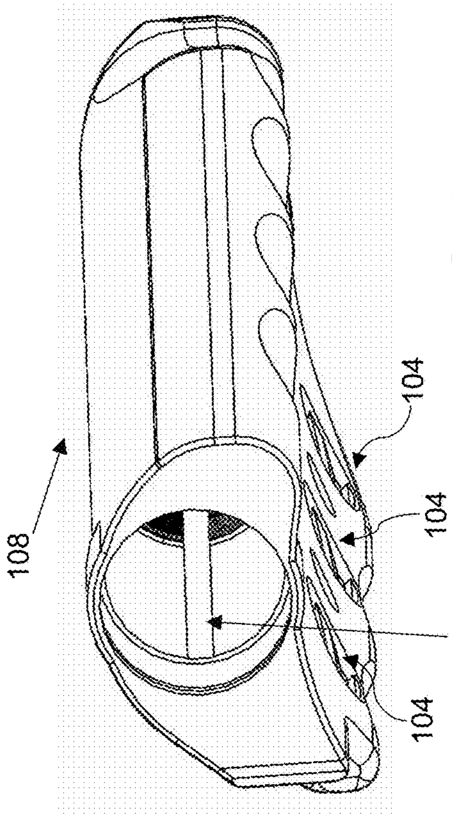
FIG. 28 shows a perspective view of the housing according to an embodiment of the disclosure.
Figure 30:
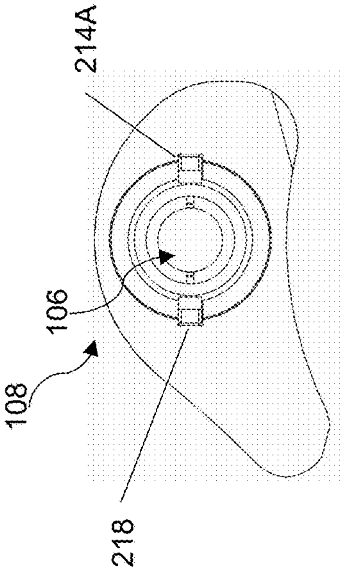
FIG. 30 shows a perspective view of the end cap according to embodiments of the disclosure.
Figure 27:
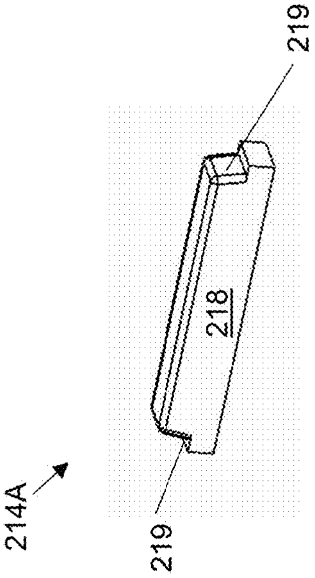
FIG. 27 shows a perspective view of the anti-rotation feature according to an embodiment of the disclosure.

In certain example implementations, as illustrated in FIGS. 7, 10, 11, 27, and 29, an anti-rotation feature 214A can include one or more anti-rotation pegs 218 extending radially from the distractor 106. The anti-rotation peg(s) 218 may be configured to mate with corresponding grooves (or, guide grooves) 220 in the second plate 108 (FIG. 10, FIG. 28). In these implementations, the anti-rotation peg(s) 218 extend along only a portion of an axial length of the distractor 106 (along axis (a)). In a particular example, one or more anti-rotation peg(s) 218 include a notch 219 at an axial end thereof. In certain cases, each anti-rotation peg(s) 218 includes a notch 219 at each axial end thereof (FIG. 27). In particular examples, the anti-rotation peg(s) 218 can sit within a slot 221 in the distractor 106 (FIG. 29), such that only a portion of the peg(s) 218 protrudes radially outward from the outer surface of the distractor 106. In various implementations, the anti-rotation peg(s) 218 has a greater axial length (along axis (a)) than a radial depth (as measured along a radial direction perpendicular to axis (a)). In certain cases, e.g., as illustrated in the partially transparent view in FIG. 26, the guide grooves 220 in the second plate 108 can extend along only a portion of the axial length of the second plate 108, e.g., providing an axial stop where the anti-rotation peg(s) 218 reaches the termination of the guide groove 220. In further implementations, as illustrated in FIG. 3, the output driver 210 can include an additional anti-rotation peg 218A on a distal end 136 thereof, e.g., for engaging a corresponding peg 190 of an anti jam feature 240 in the second plate 108. In other embodiments, the output driver 210 may include one or more additional anti-rotation peg(s) 218 on the distal end 136 thereof, e.g., for engaging one or more corresponding slot(s) 221 in the second plate 108.

In additional example implementations, as illustrated in FIGS. 10 and 26, an anti-rotation feature 214B can include a set of grooves (or, threads) 222 on the second plate 108 that are configured to resist rotation of a first set of grooves (or, threads) 224 on the distractor 106. In these cases, grooves 222 and grooves 224 are configured to interface (e.g., mate) and limit rotation of the second plate 108 relative to the distractor 106. As shown in FIG. 26, the grooves 222 can be located along only a portion of the axial extent of the second plate 108, e.g., to limit axial length when the corresponding grooves 224 on distractor 106 reach that axial location.

Figure 7:
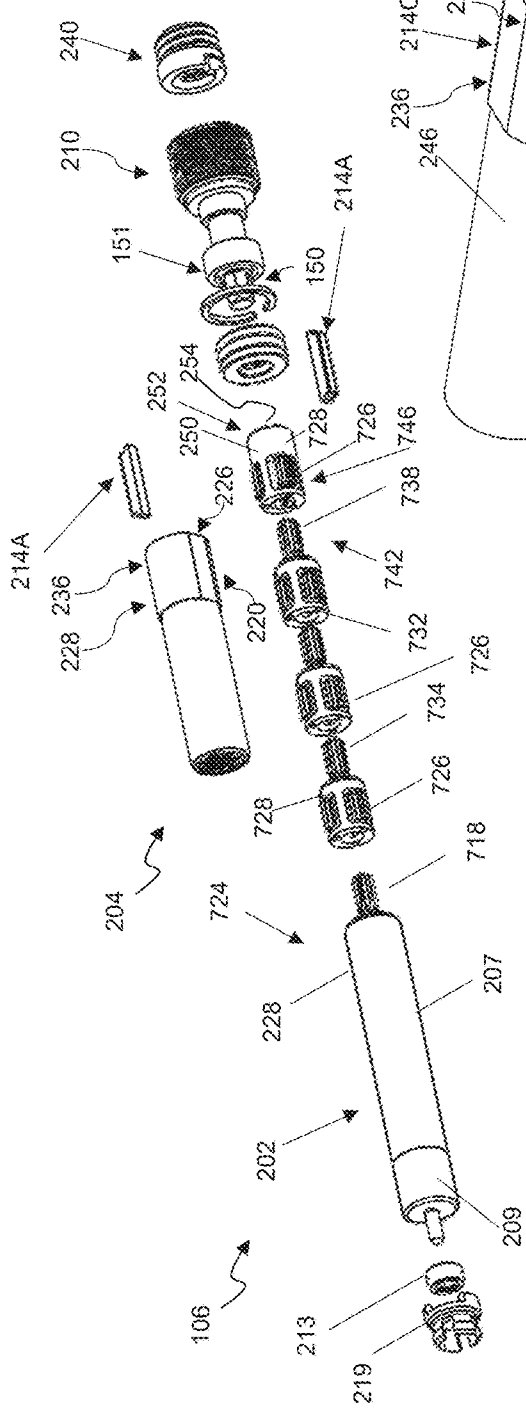
FIG. 7 shows an exploded view of a gear assembly and magnet assembly according to embodiments of the disclosure.
Figure 8:
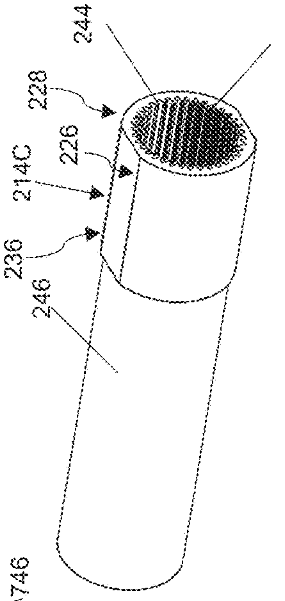
FIG. 8 shows an enlarged perspective view of a ring gear according to embodiments of the disclosure.

In further implementations, as illustrated in FIGS. 7 and 8, an anti-rotation feature 214C includes at least one straight region 226 at an interface 228 between the second plate 108 and the distractor 106. In these cases, the second plate 108 and/or the distractor 106 includes a straight region 226 at the interface 228. In particular examples, the second plate 108 and the distractor 106 each include a straight region 226 at the interface 228, such that the straight regions 226 complement one another to limit rotation of the second plate 108 relative to the distractor 106. In some cases, the straight region 226 is located along an outer surface of a ring gear 246, further described herein.

Figure 29:
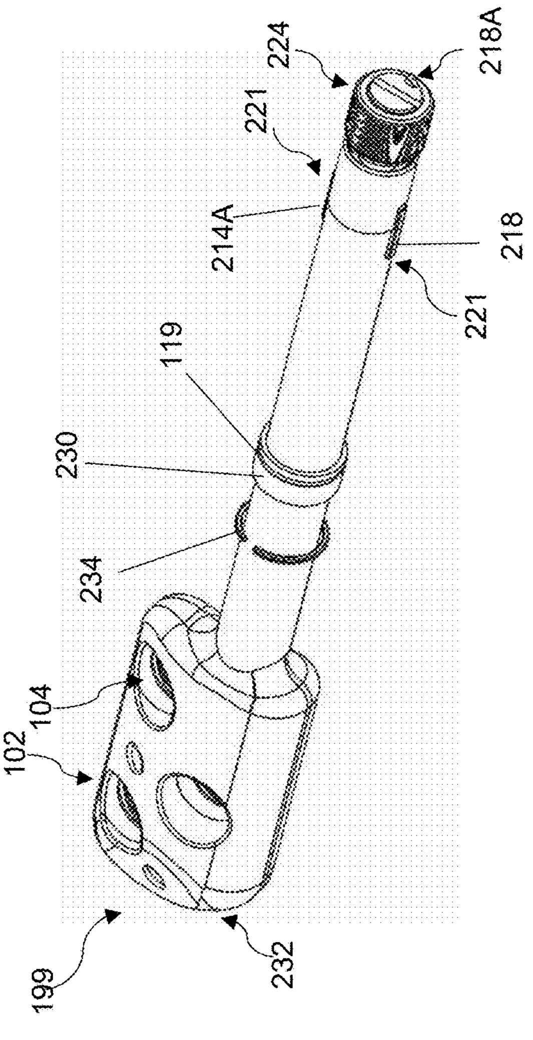
FIG. 29 shows a cross-sectional top view of the device taken along line C-C of FIG. 2 according to an embodiment of the disclosure.

In certain implementations, such as illustrated in FIGS. 10 and 29, the distractor 106 further includes an end cap 230 (e.g., closer to its proximal end 232) for limiting an extent to which the second plate 108 can translate relative to the first plate 102. That is, the end cap 230 can limit translation of the second plate 108 relative to the first plate 102. In some examples, a retaining ring 234 extends at least partially circumferentially about the distractor 106, and is located axially between the end cap 230 and the first plate 102. In such cases, the retaining ring 234 can aid in keeping the end cap 230 and distraction rod 106 from separating or coming apart from first plate 102. In certain cases, an additional retaining ring 234A is located axially between the drive system 200 and the output driver 210. Retaining ring 234A can be located in an annular slot 235 about the distractor 106, e.g., at the terminal end of the body of the distractor 106.

Figure 4:
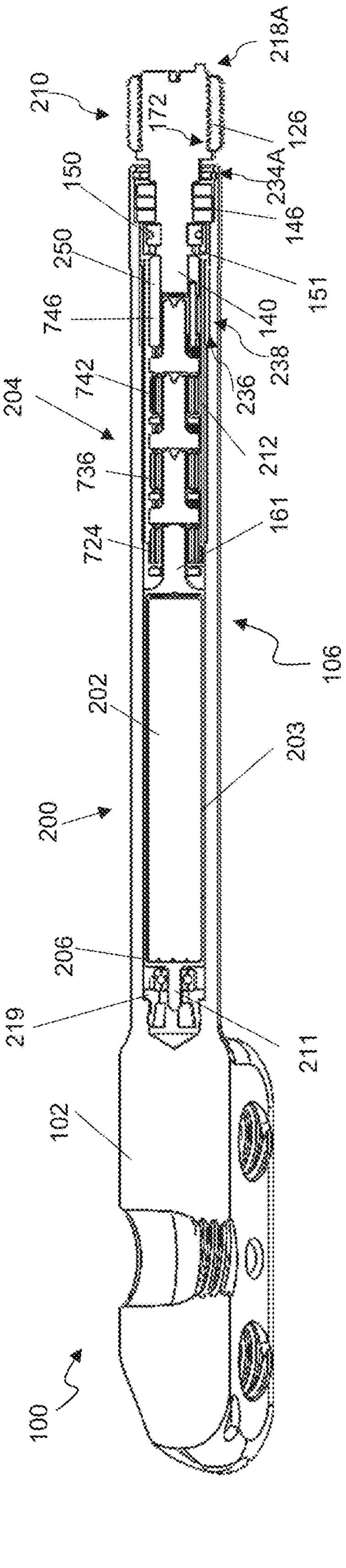
FIG. 4 shows an enlarged view of box 4 of FIG. 2.

In still further implementations, as illustrated in FIGS. 4, 7, and 8, a portion of the outer dimension 236 (e.g., outer surface) of the distractor 106 can have a non-circular cross-section. In particular cases, the outer dimension 236 of the ring gear 246 (FIGS. 4, 7, 8, and 25) can include the non-circular cross-section, e.g., one or more straight, or flat, regions 226. In additional implementations, the second plate 108 has an inner dimension (e.g., inner surface) 238 with a non-circular cross-section (FIG. 4). According to certain implementations, the (non-circular cross-section of the) outer dimension 236 of distractor 106 and the (non-circular cross-section of the) inner dimension 238 of the second plate 108 cooperate to limit rotation of the second plate 108 during actuation of the drive system 200. In particular implementations, the flat regions 226 on the ring gear 246 interact with flat sections of the anti-rotation feature 214A to limit rotation of the ring gear 246 relative to the distractor 106.

Figure 6:
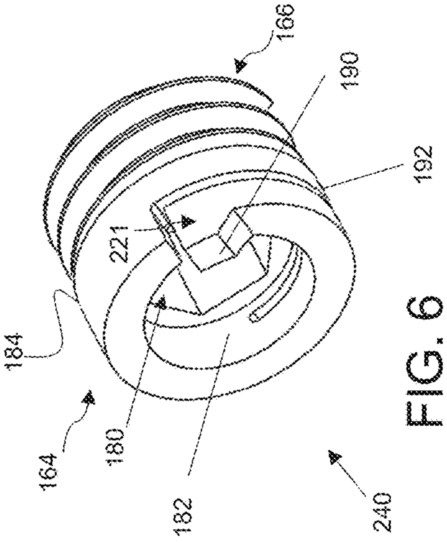
FIG. 6 show an enlarged exploded view of an anti jam retainer and ring according to embodiments of the disclosure.

In some examples, as noted herein, the implant 100 (e.g., second plate 108) includes an internal anti jam feature 240, e.g., a peg 190 adjacent to slot 221 (which acts as a spring arm), for example, to create and store spring force for retraction to overcome static surface friction (or, sticking, or jamming) between the distractor 106 and the second plate 108 during actuation of the drive system 200. FIG. 6 shows a portion of the anti-jam feature 240 separated from the second plate 108, and illustrating the face of the peg 190 for receiving the corresponding mating face of peg 218A. The anti jam feature 240 can further include a retainer clip 150 (FIG. 5), e.g., to receive the second end 136 of the output driver 210. A capture sleeve 151 is located adjacent to the retainer clip 150 for at least partially containing the retainer clip 150. The retainer ring capture sleeve 151 also includes a collar 153 for substantially surrounding the retainer clip 150 and maintaining a position of the retainer clip 150 relative to the output driver 210 (FIG. 2). The anti jam feature 240 may be configured to prevent the distractor 106 from jamming or stalling in a fully retracted state. For example, the anti jam feature 240 may provide a spring force to overcome a friction force of the distractor 106 in a scenario where the distractor 106 jams or stalls. In various implementations, the peg 190 is configured to engage the peg 218A from output driver 210, and can have a profile shaped to restrict movement of the peg 218A relative to the anti jam feature 240. As shown in the example in FIGS. 6 and 7, the anti jam feature 240 includes a substantially circular anti jam retainer 164 and a semi-circular anti jam ring 166 coupled thereto. The anti jam retainer 164 includes an opening 180 having slot 221 with a keyed shape (e.g., hex shape) to allow installing via mating threads in the housing or distal cap 120. This allows the anti jam retainer 164 to be rotationally fixed relative to the housing or distal cap 120 as the output driver 210 rotates. As shown in this example, the anti jam retainer 164 includes a collar 182 with an internal surface that is substantially circular and does not have a keyed shape like opening 180 (e.g., hex-shaped opening). The collar 182 includes a groove (e.g., a set of threads) 184 formed in an outer surface thereof. In addition, the anti jam ring 166 can include a tab and/or a projection 190 extending axially and radially therefrom. In certain cases, a spring cut 192 in the anti jam retainer 164 provides enhanced spring force in the anti-jam feature 240. The anti-jam retainer 164 can prevent the distractor 106 from jamming or stalling in a fully retracted state. For example, a distractor 106 may become jammed in a fully retracted state due to frictional forces in the retracted state. Therefore, a torque greater than a torque provided by the external adjustment device 400 (FIG. 21) may be needed to jumpstart or overcome the frictional forces in a jammed state. As a result, the anti-jam feature provides a built-in mechanism within the implant 100 to provide an additional force above and beyond that which is provided by the external adjustment device 400 thereby providing such a jumpstart force. Specifically, in a jammed state, the external adjustment device 400 causes the output driver 210 (via the driver 202 and gear system 204 (FIG. 4)) to rotate but the distractor 106 does not move axially due to being jammed. In the jammed state, peg 218A (FIG. 29) on the end of the distractor 106 engages with the tab 190 of the anti jam ring 166. As the external adjustment device 400 causes the distractor 106 to rotate, and with the anti-jam ring 166 fixed to the housing or distal cap, the tab 218A on the output driver 210 contacts the tab 190 on the anti-jam ring 166 to cause the anti-jam tab 190 to spring out to the housing ID thereby providing sufficient force to overcome the frictional forces holding the distractor 106 in the jammed state. As a result, this causes the distractor 106 to become unjammed.

In additional implementations, as shown in FIG. 4, an anti jam retainer 164 and retainer clip 150 can be located axially between the gear system 204 and the distal end of the output driver 210. The anti jam retainer 164 can provide additional, or alternative anti jam functions as the anti jam feature 240 illustrated in FIG. 7 (for engaging the distal end 136 of output driver 210), as described in U.S. patent application Ser. No. 17/806,552 ("Distraction Loss Magnet On-Off Mechanism," filed on Jun. 13, 2022) and Patent Cooperation Treaty (PCT) Patent Application PCT/US2021/041701 (Extramedullary Device, System and Methods, filed on Jul. 14, 2021), each of which is incorporated by reference in its entirety.

Turning to FIGS. 2 and 4, during operation the distractor 106 may axially translate relative to the second plate 108 by means of the output driver 210. The output driver 210 may be configured to rotate a nut 126 positioned between the output driver 210 and the second plate 108. The nut 126 may be secured to output drive threads 172 of the distractor 106 in which the output driver 210 is disposed. The output driver 210 may be rotatably coupled to the driver 202. Driver 202 may include a rotatable permanent magnet (e.g., a cylindrical permanent magnet) configured to be rotated by an externally applied magnetic field. An external adjustment device 400 (FIG. 21) may be configured to actuate rotation of the driver 202 in either of a first direction or a second direction, which in turn effectuates rotation of the output driver 210. Rotating output driver 210 then translates into axial movement of the distractor 106 relative to the second plate 108. As shown in FIG. 3, the output driver 210 includes a shaft 132 having a first end 134 and a second end 136. The first end 134 of the shaft 132 is configured to be coupled with the driver 202 (FIGS. 2 and 4), e.g., via gear system 204. The first end 134 may include a first end portion 138 having an external keyed surface 140 (e.g., a hex shape) and a second portion 142 axially separated from the first end portion 138. The first end portion 138 is configured to be engaged within an opening 252 (FIG. 7) of the drive stage 250 (FIGS. 4 and 7) of gear system (or, gear assembly) 204 (FIGS. 2, 4, and 7) as will be described herein. The second portion 142 is configured to be engaged with at least one thrust bearing 146 (one shown in FIG. 4) positioned adjacent to at least one retainer clip 150 (one shown). In some examples, the thrust bearings 146 each consist of two separate races with ball bearings between the two races. The thrust bearings 146 are configured to transmit high compressive forces during rotation of the output driver 210 and axial movement of the distractor 106 relative thereto. In some cases, the distractor 106 may include an internal projection and/or ledge disposed between the thrust bearings 146.

Figure 5:
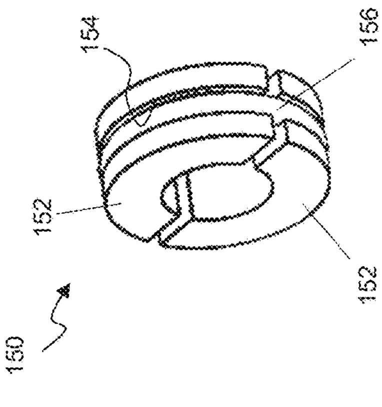
FIG. 5 show an enlarged perspective view of a retainer clip according to embodiments of the disclosure.

Returning to FIG. 3, disposed between the first end portion 138 and the second end portion 142, the output driver 210 is recessed such that there is a smaller diameter portion 148. The smaller diameter portion 148 is sized and shaped to accommodate and/or engage with a retainer clip 150 (FIGS. 4-5) such that the retainer clip 150 is disposed within the recess defined by the smaller diameter portion 148 between first and second keyed portions 138, 142. FIG. 5 shows an enlarged view of the retainer clip 150. As shown the retainer clip 150 includes two separate arcuate members 152. Alternatively, the retainer clip 150 may include a single substantially cylindrical member 152. Member(s) 152 include a recess 154 for seating of an o-ring 156 therein. The output driver 210 can also include a step 170 from the smaller diameter portion 162 to a larger diameter portion 172. This larger diameter portion 172 is at least partially threaded and at least partially surrounded by the nut 126 (FIGS. 2 and 4) to facilitate axial movement of the distractor 106 relative to the second plate 108.

Returning to FIG. 4, a drive system 200 is located within the distractor 106. and may include the driver 202 such as, for example, a cylindrical, radially-poled permanent magnet contained within a housing 203 having an end cap 206. In a particular example, the (e.g., magnetic) driver 202 may include rare earth magnet materials, such as Neodymium-Iron-Boron. The driver 202 may include a protective Phenolic coating and may be held statically within the housing 203 and end cap 206 by epoxy or other adhesive. The housing 203, end cap 206 and epoxy can form a seal to further protect the driver 202. The housing 203 may also be welded to end cap 206 to create a hermetic seal. To aid in manufacturing and assembly, the housing 203 may include separate magnet cups 207, 209 (FIG. 7) for housing the driver (e.g., magnet) 202 therein. The end cap 206 can include a cylindrical extension or axle 211 which fits within the inner diameter of a radial bearing 213, allowing for low friction rotation. The outer diameter of radial bearing 213 can fit within a cavity (FIG. 9) of an anti-distraction loss feature (or, brake) 219 as seen, for example, in FIG. 4.

Figure 9:
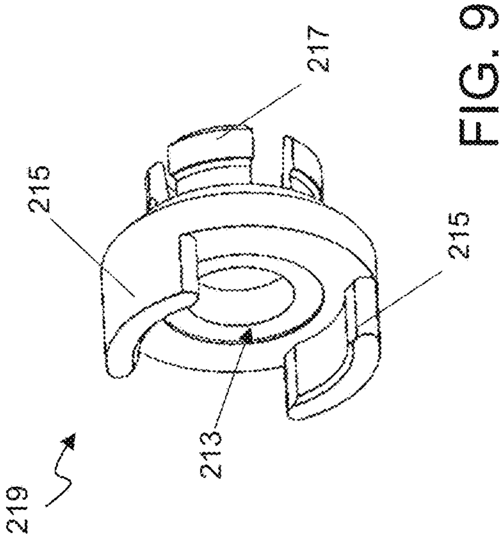
FIG. 9 shows an enlarged perspective view of a brake for an implant according to embodiments of the disclosure.

An enlarged view of the brake (e.g., magnet brake) 219 is shown in FIG. 9. The brake 219 prevents the implant 100 from being accidentally adjusted by movements of the patient. The brake 219 is positioned proximate and axially spaced from the drive system 200 within the implant 100. In some examples, the brake 219 is made from a magnetically permeable material, such as 400 series stainless steel. The brake 219 can be generally cylindrical in shape having two spaced apart tabs and/or projections 215 separated by gaps. When the implant 100 is not being adjusted (e.g., using an external adjustment device), the magnetic poles of the radially-poled cylindrical magnet are magnetically attracted to the tabs 215. However, when the drive system 200 is forced to rotate due to the effect of a sufficiently large rotating magnetic field on the radially-poled cylindrical magnet (e.g., in driver 202), the drive system 200 overcomes the smaller attractions of the tabs 215. The brake 219 can also include flanged extension and/or flanged extension fingers 217 for engaging with the end cap 120 and/or second plate 108. Additional details of the brake can be found in U.S. Pat. Pub. 20190015138, filed Jul. 26, 2018, which is incorporated herein by reference as if set forth in its entirety. Other brakes such as those disclosed in U.S. Pat. No. 8,734,488 filed Aug. 4, 2011, and U.S. application Ser. No. 13/525,058 filed Jun. 15, 2012, each of which are incorporated herein by reference as if set forth in its entirety.

As shown in FIGS. 2, 4, and 7, the driver 202 is coupled to gear system (or, assembly) 204. The gear system 204 is configured to couple the output driver 210 to the drive system 200, e.g., the driver 202. In certain examples, referring to FIG. 7, the driver (e.g., magnetic driver) 202 terminates at an opposing end in a first sun gear 718 which is formed integrally with the housing 203. Alternatively, the first sun gear 718 may include a separate component configured to couple to the magnet housing 203, for example by welding. First sun gear 718 turns with rotation of driver 202 (in a 1:1 fashion) upon application of an externally applied magnetic field. The first sun gear 718 is configured to insert within an opening of, and rotatably engage with, a first gear stage 724 having one or more planetary gears 726 that are rotatably held in a frame 728 by an axle(s) 732. As shown in FIG. 7, the first gear stage 724 includes three planetary gears 726 which are rotatably held in the frame 728 by axles 732. Second sun gear 734, which is the output of the first gear stage 724, turns with frame 728. The identical components exist in second gear stage 736, which outputs to a third sun gear 738, and third gear stage 742, which outputs to a fourth gear stage 746, which terminates in a drive stage 250. The drive stage 250 is positioned about the gear system 204 furthest from the driver 202. Along the length that the gear stages 724, 736, 742, 746 extend, an inner wall 244 of a ring gear 246 (as seen in FIG. 8) has internal teeth 248 along which the externally extending teeth of the planetary gears 726 engage while rotating. In the example of FIG. 7, each of the four gear stages illustrated has a 4:1 gear ratio, such that the drive stage 250 turns once for every 256 turns of the driver 202. In other embodiments, the gear stages 724, 736, 742, 746 may include a different gear ratio.

The frame 728 of the fourth gear stage 746 includes the drive stage 250. The drive stage 250 includes an opening 252 having a keyed internal surface 254. The keyed internal surface 254 is configured to matingly engage with a keyed external surface 140 of the first end 134 of the output driver 210. The engagement of the keyed surfaces 254, 140 prevent rotation of output driver 210 and drive stage 250 relative to each other. The keyed surfaces 254, 140 may be, for example, a hex shape. However, other shapes configured to prevent rotation of the output driver 210 relative to the drive stage 250 are also contemplated by the disclosure. To further maintain the output driver 210 within the drive stage 250, a first retainer clip 150 may be provided within the opening 252 of the drive stage 250 and at least partially surround the output driver 210 proximal to the keyed external surface 140. Specifically, the retainer clip 150 can be positioned about the smaller diameter portion 148 (FIG. 3) within the central (e.g., axial) opening of the capture sleeve 151.

In some examples, the torque applied on the drive system 200 by the action of the rotating magnetic field on the (e.g., magnetic) driver 202, is therefore augmented on the order of 64 times in terms of the turning torque of the output driver 210. This allows the distractor 106 to be able to move with high precision. Because of the 64:1 gear ratio, the implant 100 is able to axially displace the bone segment coupled to the distractor 106 against severe resisting forces, for example those created by soft tissue.

The thrust bearing(s) 146 serves to protect the drive system 200 and the gear system 204 of the drive from any significant compressive or tensile stresses. When there is a compressive force on the device, for example, when distracting a bone, and thus resisting the tensile strength of the soft tissues, the thrust bearing(s) 146 abuts against retainer clip(s) 150 and/or ledge between thrust bearings. Additionally, though the implant 100 is not as often used for pulling bones together, there may be some applications where this is desired. For example, in certain compressive applications it is the goal to hold two fractured sections of a bone together. Because the bone may have fracture in a non-uniform or shattered pattern, it may be difficult to determine the desired length of the implant 100 until after it is implanted and fully attached. In these situations, it can be easy to misjudge the length, and so a gap may exist between the separate sections or fragments of bone. By placing a slightly extended implant 100 and securing it, the implant 100 may be retracted magnetically, after it has been secured within the bone fragments, so that it applies the desired compression between the two fragments. In these compressive applications, there would be tensile force on the implant 100 and the thrust bearing(s) 146 would abut against the retainer clip(s) 150 or ledge. In both situations, the thrust bearings 146 and the ledge take the large stresses, not the drive system 200 or gear system 204 of the drive system.

Figure 17:
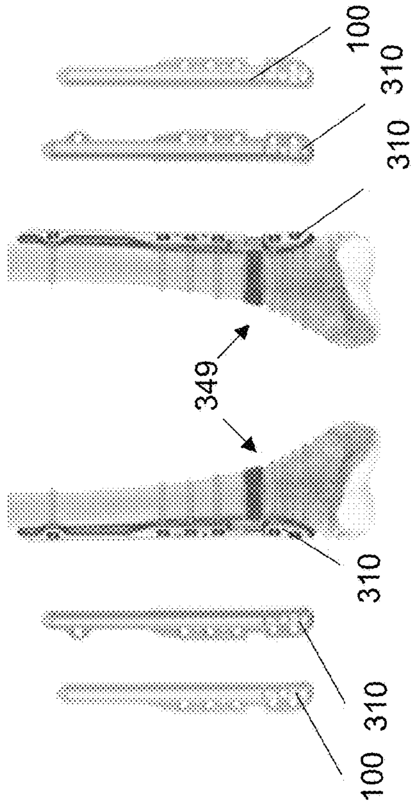
FIG. 17 shows various embodiments of an extramedullary distraction and compression device according to the disclosure that can be attached to a distal end of a femur bone.

Returning now to FIG. 1, the implant 100 can include pin holes 272 for receiving pins to help aid in holding the implant 100 against the bone during implantation of the implant 100 as is known in the art. As shown, the pin holes 272 can be positioned at various positions about the first plate 102, the second plate 108, and/or the end cap 120. Further, the implant 100 can include any number of fixation apertures 104 positioned within the first plate 102, second plate 108, and/or the end cap 120 without departing from aspects of the disclosure. In some embodiments, the implant 100 of FIG. 1 can be affixed to a proximal portion of the bone, e.g., a proximal end of a femur (FIG. 15), or to a distal portion of the bone, e.g., a distal end of a femur (FIG. 17). Further, the implant 100 can be positioned antegrade or retrograde.

Figure 12:
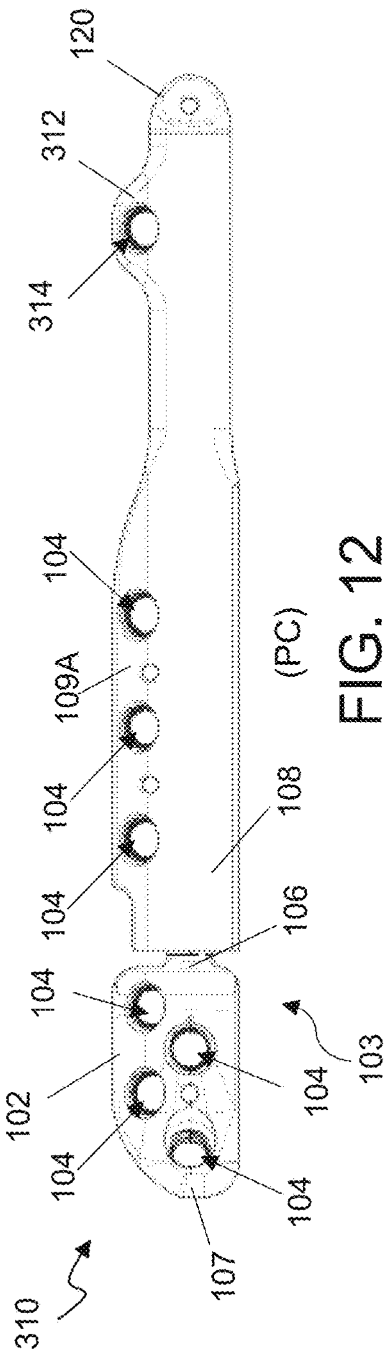
FIG. 12 shows a top-down view of an extramedullary distraction and compression device according to another embodiment of the disclosure.
Figure 13:
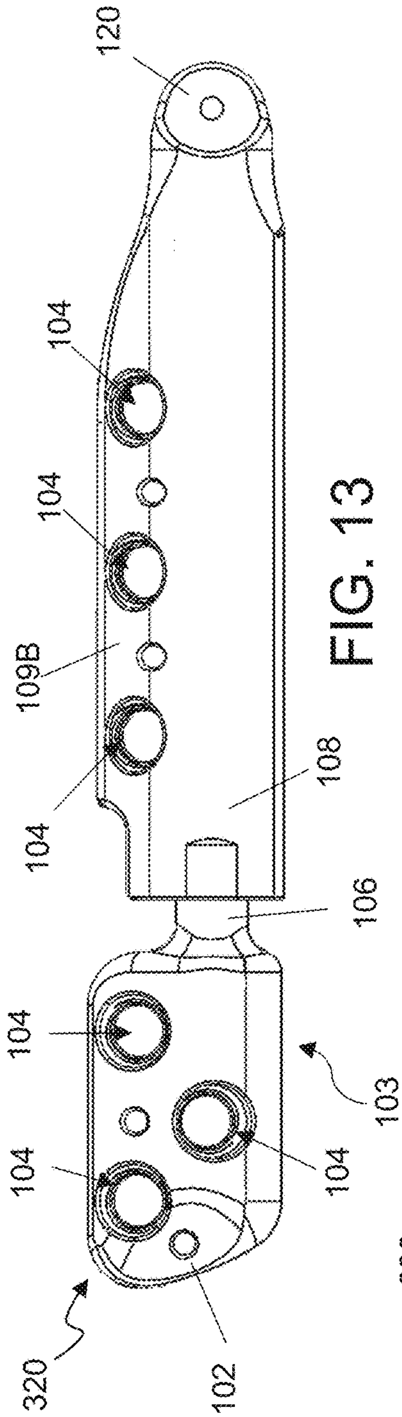
FIG. 13 shows a top-down view of an extramedullary distraction and compression device according to another embodiment of the disclosure.
Figure 14:
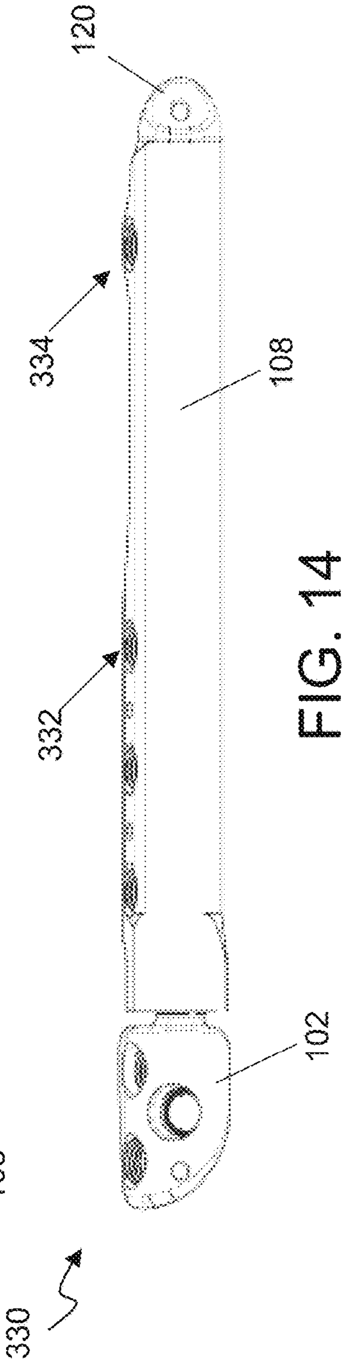
FIG. 14 shows a side view of an extramedullary distraction and compression device according to another embodiment of the disclosure.

FIGS. 12-14 show extramedullary distraction and compression devices according to other embodiments of the disclosure. Specifically, the implants 310, 320, 330 of FIGS. 12-14 differ from implant 100 (FIG. 1) in their outer configuration or dimension. Further, it is to be understood that the overall lengths of the distractor 106 and/or housing 103 can be adjusted depending on the particular application and/or bone that the implant 100, 310, 320, 330 is being affixed to. The internal components of the implants 310, 320, 330 may be the same as, or substantially similar to, the implant 100 and duplicative description of which has been omitted for brevity. The differing outer configurations or dimensions may be determined by the location on the bone which the implant 100, 310, 320, 330 is to be implanted and the size or length of the bone.

Figure 18:
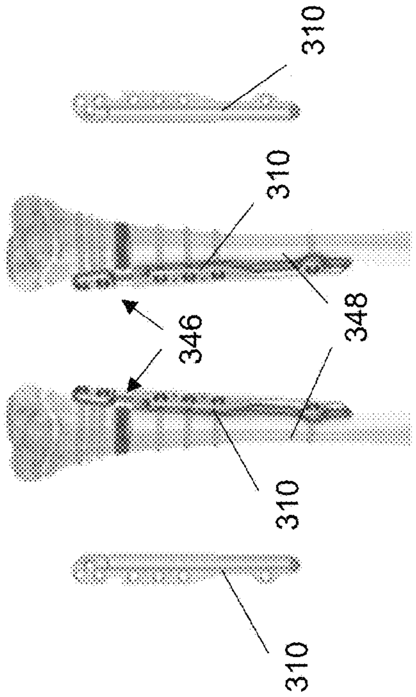
FIG. 18 shows various embodiments of an extramedullary distraction and compression device according to embodiments of the disclosure that can be attached to a proximal end of the posterior-medial tibia bone.

For example, implant 310 of FIG. 12 has substantially the same outer configuration as implant 100 (FIG. 1), however, the implant 310 includes a second bulge 312 spaced from the bulge 109A in second plate 108 that includes an additional fixation aperture 314. Like implant 100, this implant 310 can also be affixed to a proximal portion of the bone, e.g., a proximal portion 342, 346 of a femur 344 (FIG. 15) or tibia 348 (FIG. 18), or to a distal portion of the bone, e.g., a distal end 349 of a femur (FIG. 17).

Figure 16:
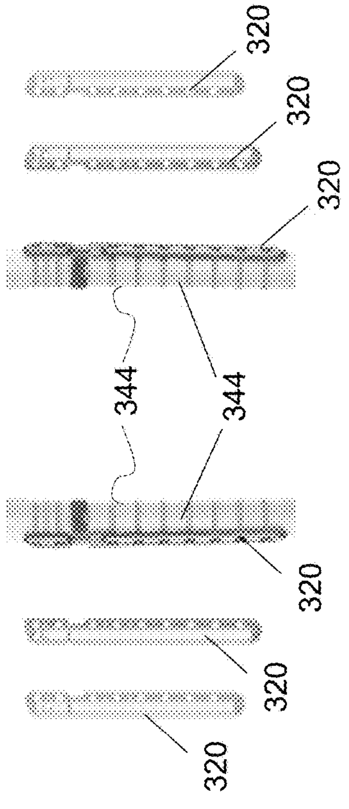
FIG. 16 shows various embodiments of an extramedullary distraction and compression device according to the disclosure that can be attached to a shaft of a femur bone.

The implant 320 according to FIG. 13 is substantially the same as implant 100 (FIG. 1), however, the bulge 109B of implant 320 extends a substantial length of the second plate 108. Further, the implant 320 may include fixation apertures 104 extending along a substantially length of the second plate 108 about the bulge 109B. This embodiment of the implant 310 may be used about the shaft of the bone, e.g., the shaft of a femur 344 as shown in FIG. 16. Further, this implant 320 can include a different number of fixation apertures 104 within the bulge 109A of the second plate 108.

The implant 330 according to FIG. 14 is substantially the same as implant 100 (FIG. 1), however, the second plate 108 of this device can be substantially curved and configured to be affixed to the proximal end 346 of a tibia 348 at a posterior-medial location on the tibia 348. For example, second plate 108 of the implant 330 can include a first fixation aperture 332 configured to be affixed at a medial portion of the tibia 348 and at least one other fixation aperture 334 configured to be affixed at a posterior portion of the tibia 348.

Figure 15:
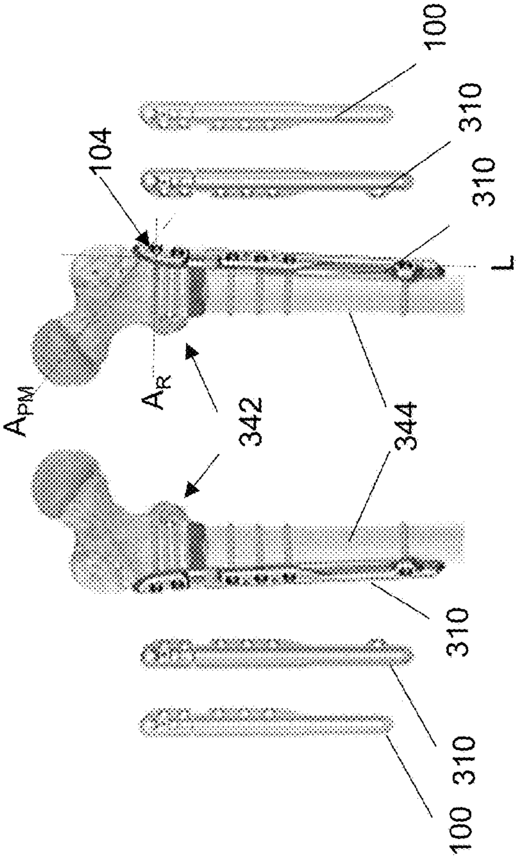
FIG. 15 shows various embodiments of an extramedullary distraction and compression device according to the disclosure that can be attached to a proximal end of a femur bone.

FIG. 15 shows examples of the implant 100, 310 that can be used at the proximal portion 342 of the femur 344. As shown, the proximal-most fixation aperture 104 is angled relative to the longitudinal axis L for the implant 100 so that a screw positioned therein is angled $A_{PM}$ and extending toward the head of the femur 344. In some embodiments, the proximal-most fixation aperture 104 is angled at an angle $A_{PM}$ of approximately 115° to approximately 125° relative to the longitudinal axis L of the implant 100 while the screws positioned within the remainder of the fixation apertures 104 extend at an angle AR of approximately 90° relative to the longitudinal axis L of the implant 100.

Turning now to FIGS. 19 and 20, examples of screws that can be used to affix the implants 100, 310, 320, 330 to bone are shown. FIG. 19 shows a non-locking screw 810. As shown, the non-locking screw 810 includes a threaded shaft 812 and a screw head 814. The screw head 814 is not threaded and substantially rounded in shape. The screw head 814 can include a recess 815 for engaging with a tool, e.g., a driver (not shown). FIG. 20 shows a locking screw 820. As shown, the locking screw 820 includes a threaded shaft 812 and a threaded screw head 816. The threaded screw head 816 can include a recess 815 for engaging with a tool, e.g., a driver. The threaded screw head 816 is configured to threadingly engage with the internal thread 112 (FIG. 2) of a fixation aperture 104 to lock an angular orientation of the locking screw 820 relative to the second plate 108 and/or the distractor 106. It is to be understood that combinations of locking and/or non-locking screws 810, 820 can be used to affix the implant 100, 310, 320, 330 to the bone without departing from aspects of the disclosure. Further, it is the be understood that combinations of threaded and non-threaded fixation apertures 104 can be used within the first plate 102, the second plate 108 and/or the distractor 106.

Figure 21:
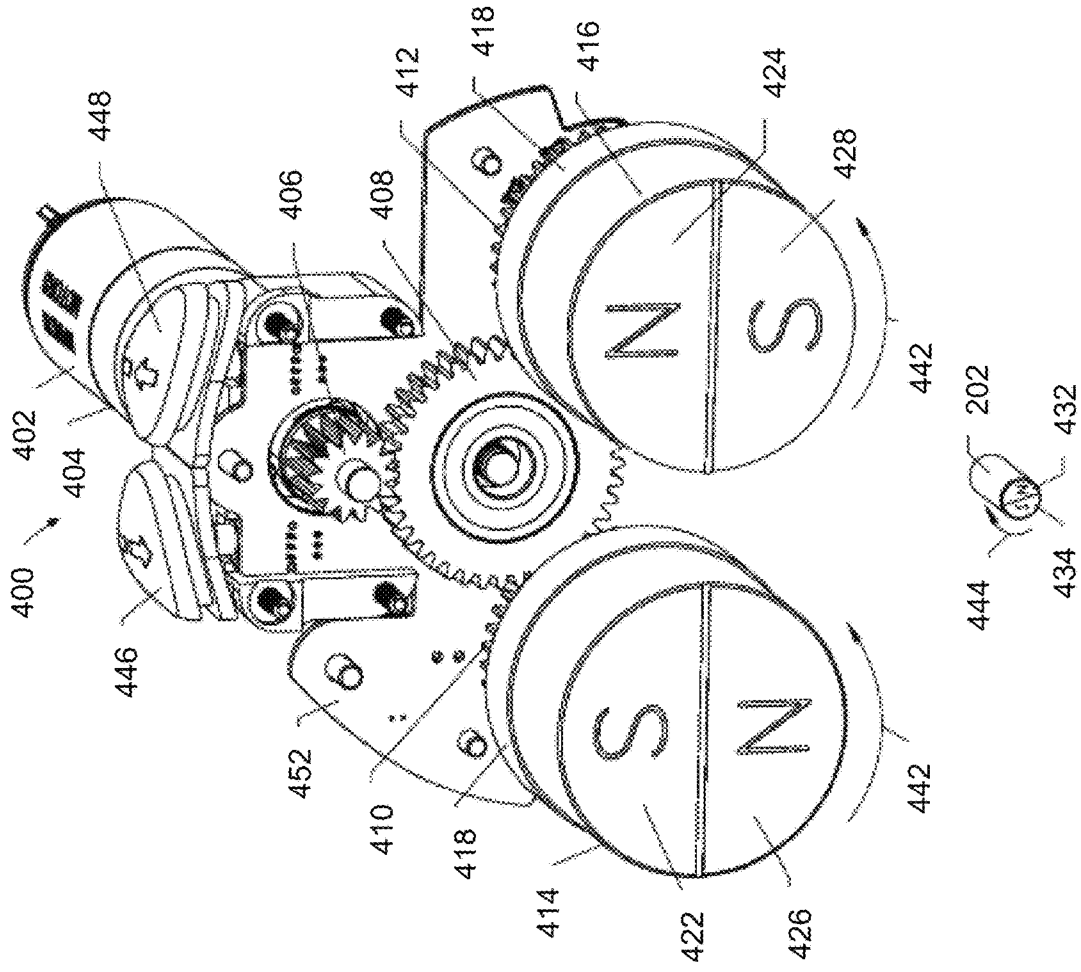
FIG. 21 shows internal components of an external adjustment device for non-invasively adjusting an extramedullary distraction and compression device according to embodiments of the disclosure.
Figure 22:
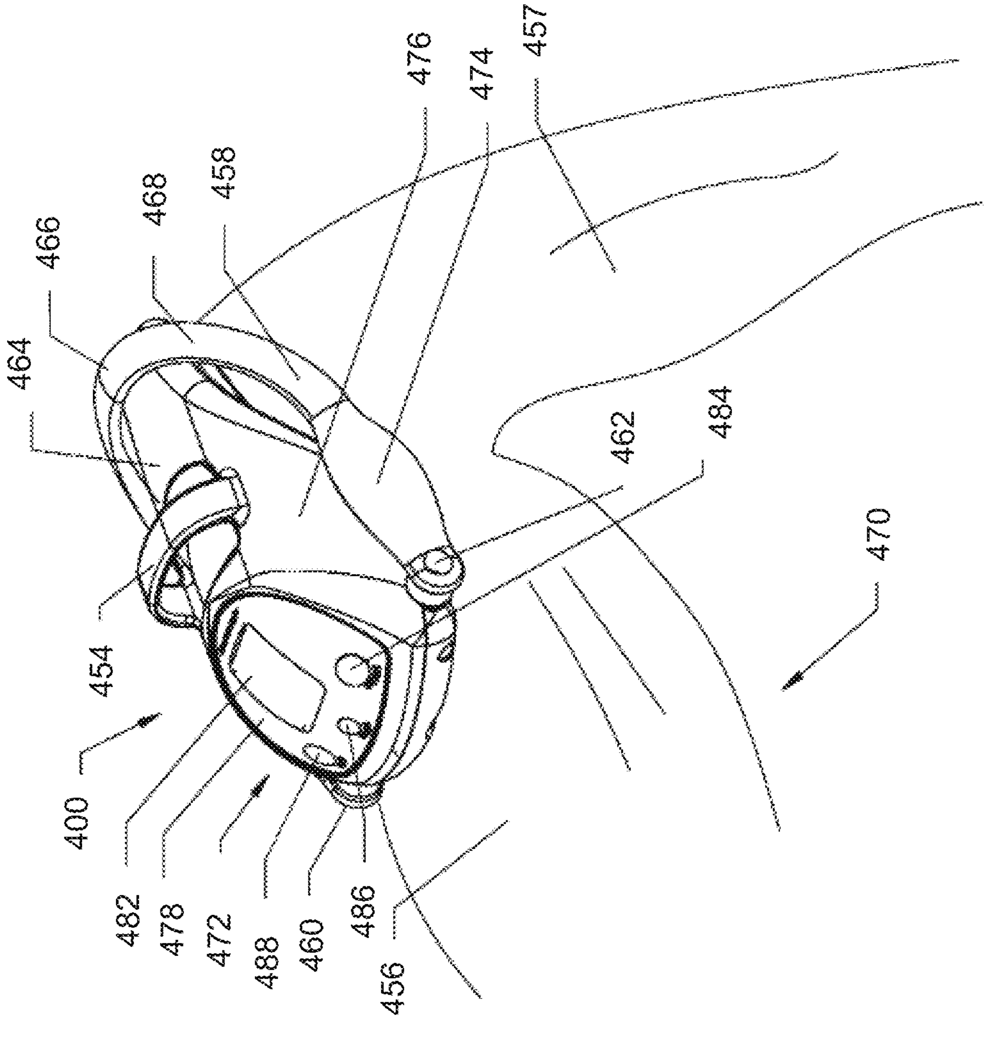
FIG. 22 shows an external adjustment device in a configuration for adjusting an extramedullary distraction and compression device according to embodiments of the disclosure implanted within the femur.
Figure 23:
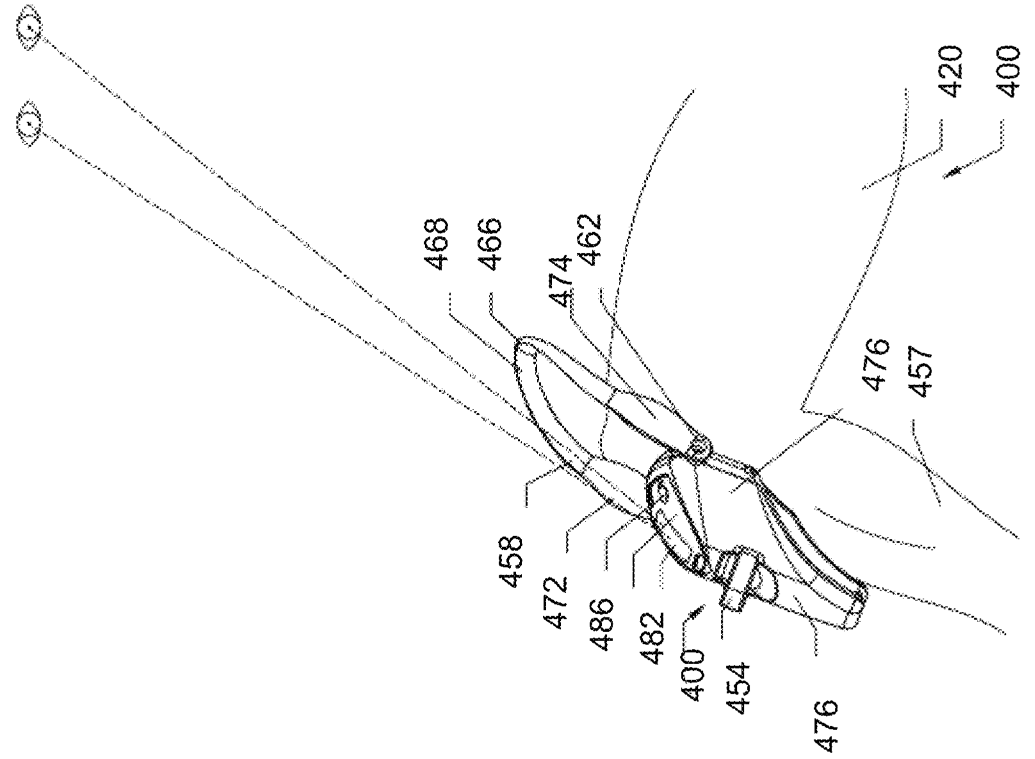
FIG. 23 shows an external adjustment device according to embodiments of the disclosure in a configuration for adjusting an extramedullary distraction and compression device implanted within the tibia.

FIGS. 21-23 illustrate an external adjustment device 400 configured for applying a moving magnetic field to allow for non-invasive adjustment of the implant 100, 310, 320, 330 (and other implants disclosed herein) by turning a driver (e.g., permanent magnet) 202 within the implant 100, 310, 320, 330, as described. FIG. 21 illustrates the internal components of the external adjustment device 400, and for clear reference, shows the driver (e.g., permanent magnet) 202 of the implant 100, 310, 320, 330, without the rest of the assembly. The internal working components of the external adjustment device 400 may, in certain embodiments, be similar to that described in U.S. Patent Application Publication No. 2012/0004494, which is incorporated by reference herein. A motor 402 with a gear box 404 outputs to a motor gear 406. Motor gear 406 engages and turns central (idler) gear 408, which has the appropriate number of teeth to turn first and second magnet gears 410, 412 at identical rotational speeds. First and second magnets 414, 416 turn in unison with first and second magnet gears 410, 412, respectively. Each magnet 414, 416 is held within a respective magnet cup 418 (shown partially). An exemplary rotational speed is 60 RPM or less. This speed range may be desired in order to limit the amount of current density induced in the body tissue and fluids, to meet international guidelines or standards. As seen in FIG. 21, the south pole 422 of the first magnet 414 is oriented the same as the north pole 424 of the second magnet 416, and likewise, the first magnet 414 has its north pole 426 oriented the same as the south pole 428 of the second magnet 416. As these two magnets 414, 416 turn synchronously together, they apply a complementary and additive moving magnetic field to the radially-poled, driver 202, having a north pole 432 and a south pole 434. Magnets having multiple north poles (for example, two) and multiple south poles (for example, two) are also contemplated in each of the devices. As the two magnets 414, 416 turn in a first rotational direction 442 (e.g., counter-clockwise), the magnetic coupling causes the driver (e.g., permanent magnet) 202 to turn in a second, opposite rotational direction 444 (e.g., clockwise). The rotational direction of the motor 402 and corresponding rotational direction of the magnets 414, 416 is controlled by buttons 446, 448. One or more circuit boards 452 contain control circuitry for both sensing rotation of the magnets 414, 416 and controlling the rotation of the magnets 414, 416.

FIGS. 22 and 23 show the external adjustment device 400 for use with an implant 100, 310, 320, 330 placed in the femur (FIG. 22) or the tibia (FIG. 23). The external adjustment device 400 has a first handle 454 for carrying or for steadying the external adjustment device 400, for example, steadying it against an upper leg 456 (as in FIG. 22) or lower leg 457 as in (FIG. 23). An adjustable handle 458 is rotationally attached to the external adjustment device 400 at pivot points 460, 462. Pivot points 460, 462 have easily lockable/unlockable mechanisms, such as a spring-loaded brake, ratchet or tightening screw, so that a desired angulation of the adjustable handle 458 in relation to housing 464 can be adjusted and locked in orientation. Adjustable handle 458 is shown in two different positions in FIGS. 22 and 23. In FIG. 22, adjustable handle 458 is set so that apex 466 of loop 468 rests against housing 464. In this position, patient 470 is able to hold onto one or both of grips 472, 474 while the adjustment procedure (for example transporting bone between 0.10 mm to 1.50 mm) is taking place. It is contemplated that the procedure could also be a lengthening procedure for a bone lengthening device or a lengthening procedure for a lengthening plate which is attached external to the bone. Turning to FIG. 23, when the bone transport implant 100, 310, 320, 330 is implanted in a tibia, the adjustable handle 458 may be changed to a position in which the patient 470 can grip onto the apex 466 so that the magnet area 476 of the external adjustment device 400 is held over the portion the implant 100, 310, 320, 330 containing the driver 202. In both cases, the patient 470 is able to clearly view control panel 478 including a display 482. In a different configuration from the two directional buttons 414, 416 in FIG. 21, the control panel 478 includes a start button 484, a stop button 486 and a mode button 488. Control circuitry contained on circuit boards 452 may be used by the surgeon to store important information related to the specific aspects of each particular patient. For example, in some patients an implant may be placed antegrade into the tibia. In other patients the implant may be placed either antegrade or retrograde about the femur. In each of these three cases, it may be desired to move the bone either from distal to proximal or from proximal to distal. By having the ability to store information of this sort that is specific to each particular patient within the external adjustment device 400, the external adjustment device 400 can be configured to direct the magnets 414, 416 to turn in the correct direction automatically, while the patient need only place the external adjustment device 400 at the desired position, and push the start button 484. The information of the maximum allowable bone transport length per day and maximum allowable bone transport length per session can also be input and stored by the surgeon for safety purposes. These may also be added via an SD card or USB device, or by wireless input. An additional feature is a camera at the portion of the external adjustment device 400 that is placed over the skin. For example, the camera may be located between first magnet 414 and second magnet 416. The skin directly over the driver (e.g., magnet) 202 may be marked with indelible ink. A live image from the camera is then displayed on the display 482 of the control panel 478, allowing the user to place the first and second magnets 414, 416 directly over the area marked on the skin. Crosshairs can be overlaid on the display 482 over the live image, allowing the user to align the mark on the skin between the crosshairs, and thus optimally place the external adjustment device 400.

Other external adjustment devices can be used to cause actuation of the distraction devices described herein. Such external adjustment devices include, for example, those described in U.S. Pat. No. 8,382,756 filed on Nov. 20, 2009, U.S. Pat. No. 9,248,043 filed Jun. 29, 2011, U.S. Pat. No. 9,078,711 filed on Jun. 6, 2012, U.S. Pat. No. 9,044,281 filed on Oct. 18, 2012, U.S. application Ser. No. 14/698,665 filed on Apr. 28, 2015, U.S. application Ser. No. 14/932,904 filed on Nov. 4, 2015, U.S. Ser. No. 16/004,099 filed on Dec. 12, 2016, and App. No. PCT/US2020/017338 filed on Feb. 7, 2020, all of which are incorporated herein by reference as if set forth in their entirety.

Figure 24:
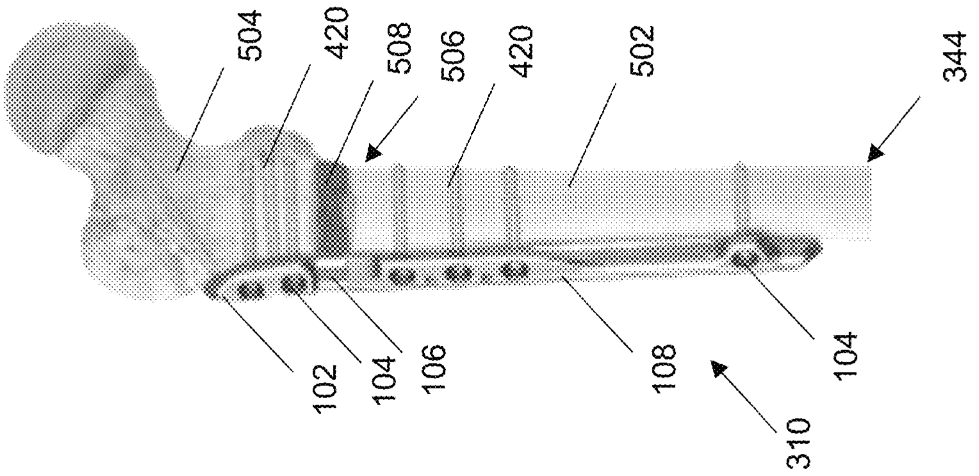
FIG. 24 shows an extramedullary distraction and compression device affixed to a bone within a limb according to embodiments of the disclosure.

Turning now to FIG. 24, aspects of the disclosure are also directed to a method for lengthening a limb. The method can include providing an extramedullary distraction and compression implant 310. FIG. 24 shows implant 310 being affixed to a proximal end of a femur 344. However, the method is equally applicable to the other implants 100, 320, 330 disclosed herein about other sites of the femur 344 of tibia 348 as was discussed relative to FIGS. 15-18. As discussed herein, the distraction implant 310 can have a second plate 108 including a first fixation aperture 104, a distractor 106, and a first plate 102 including a second fixation aperture 104. The distractor 106 is configured to distract or retract to move the first plate 102 relative to the second plate 108. The method also includes attaching the second plate 108 to a bone within the limb, e.g., femur 344, at a first location 502 by inserting at least one screw, e.g., a locking screw 420 (FIG. 20), within at least one fixation aperture 104 and attaching the distractor 106 to the bone at a second location 504 by inserting at least one screw, e.g., a locking screw 420, within at least one fixation aperture 104. As shown and described herein, the implant 310 can have any number of screw holes such that more than one screw can be used to affix the implant 310 to the bone. Further, it is to be understood that combinations of locking screws and non-locking screws can be used to affix the implant 310 to the bone. Where locking screws are used to affix the implant 100 to bone, it may be desirable to affix the implant 100 so that the device does not bottom-out directly onto the bone so that there is some space between the bone and portions of the implant 100. This allows compensation for lateral movement between the two bone sections as the two bone sections move relative to one another. Prior to affixing the implant 310 to the bone, the method can include creating an osteotomy 506 between the first and second locations 502, 504.

Further, once the implant 310 is affixed to the bone, an external adjustment device 400 can be used to actuate the implant 310 to cause the distractor 106 to move relative to the second plate 108, thereby causing the first bone location 502 to move relative to the second bone location 504. Specifically, the generation of a magnetic field from at least one magnet of the external adjustment device 400 causes rotation of the drive system 200 within the implant 310 which in turn causes the output driver 210 to rotate. As the output driver 210 rotates, the output driver 210 interacts with the nut 126 causing the second plate 108 to translate relative to the first plate 102. The translation of the second plate 108 causes distraction of the bone attached thereto and in turn causes growth of new bone 508 (or osteogenesis) about the osteotomy site 506. During the actuating, an angular orientation of the locking screw(s) 420 relative to the second plate 108 is/are maintained and an angular orientation of the locking screw(s) 420 relative to the first plate 102 is/are maintained due to the threaded screw head 416 (FIG. 20) engaging with threads 112 (FIG. 1) of the screw fixation aperture 104.

Figure 31:
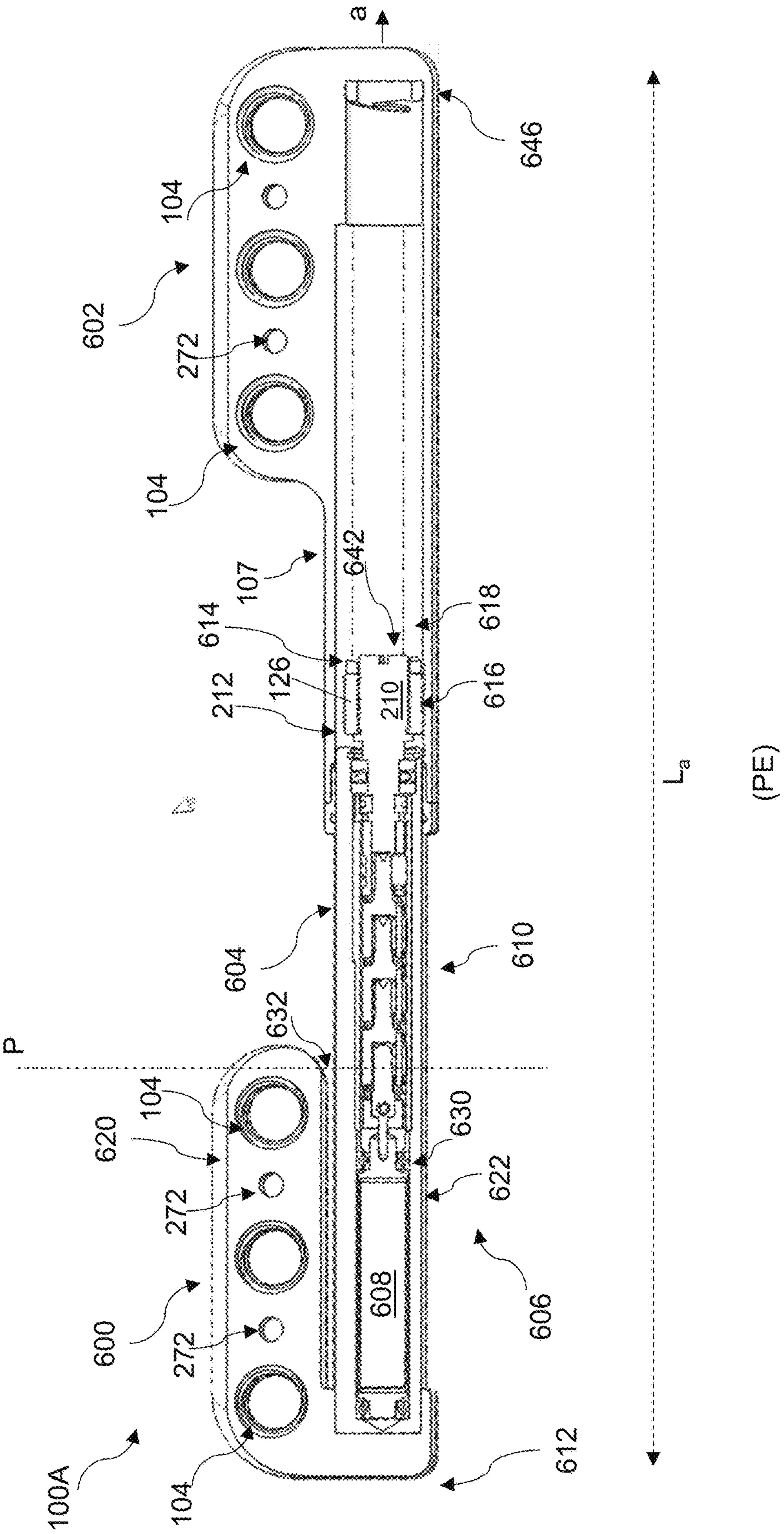
FIG. 31 shows a partial cross-section of an implant according to various additional embodiments of the disclosure.
Figure 32:
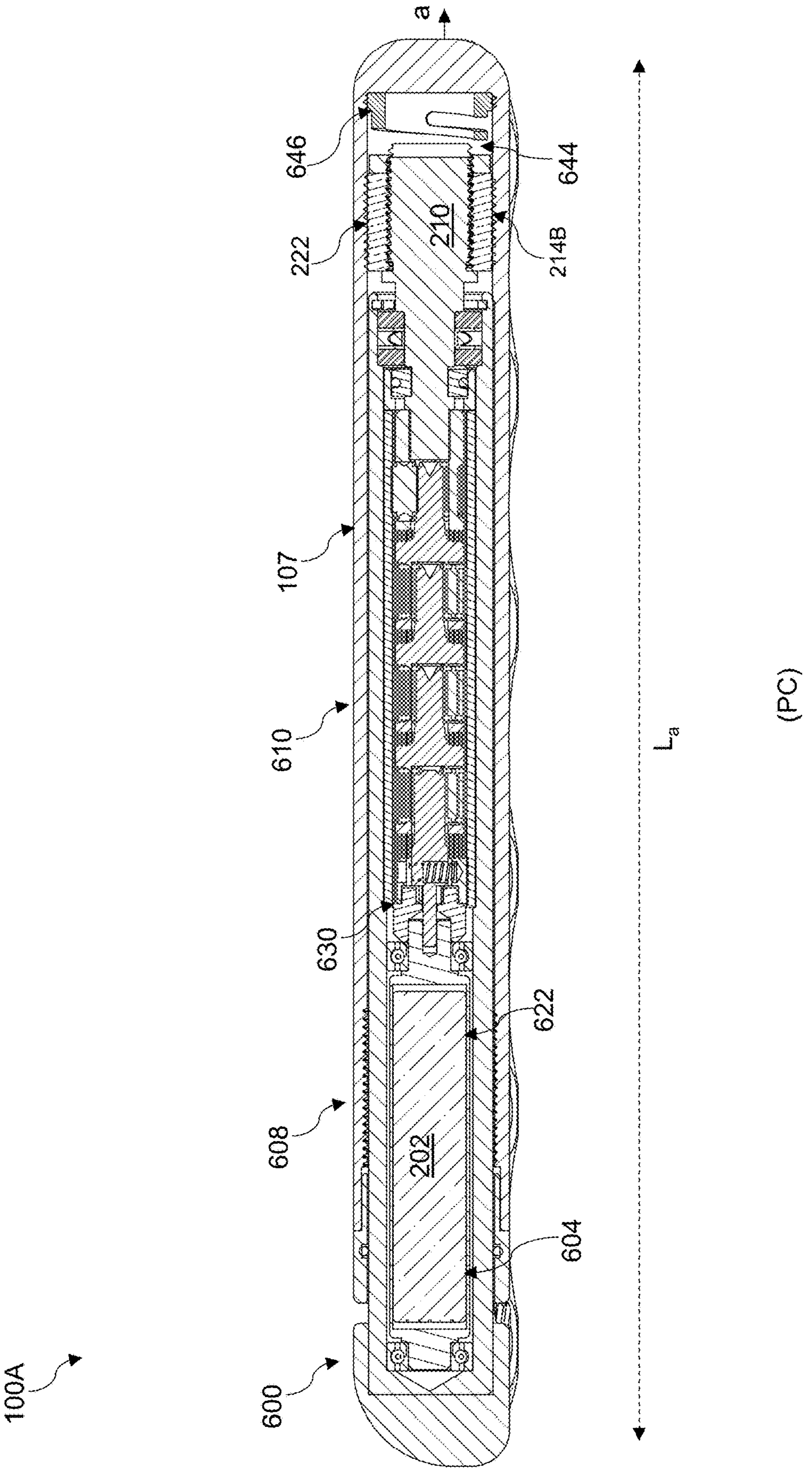
FIG. 32 shows an additional cross-section of the implant of FIG. 31.

In certain additional implementations, as illustrated in FIG. 31, an implant 100A is shown that is configured to move bone in a patient's body. Implant 100A is illustrated in a fully extended position (PE) in FIG. 31, and in a fully closed position (in cross-section) in FIG. 32 (PC), similar to the closed position of implants 100, and 310-330, illustrated in FIGS. 1 and 12-14. It is understood that in various implementations, implant 100A is suitable for use in moving bone in any manner described with reference to implant 100 (FIG. 1). Further, similarly labeled components between implant 100 and implant 100A are understood to be substantially similar components. In some cases, the implant 100A includes a first portion 600 that is configured to be attached to a bone at a first location, e.g., via one or more holes (or fixation apertures) 104 for receiving a bone anchor. In these cases, a second portion 602 of the implant 100A is configured to be attached to the bone at a second location, e.g., via one or more holes (or fixation apertures) 104. As described in more detail, below, one or more aspects of the implant 100A (or any implant described herein) can be configured to be modular (see, e.g., FIG. 38). In particular examples, the first portion 600 and the second portion 602 are first and second plates, respectively. An internal distraction component (also called a distractor) 604 extends from the first portion 600 and is at least partially contained within the second portion 602. The internal distraction component 604 can house a drive system 606, which can be similar to drive system 200 described with reference to FIG. 1. In certain cases, the drive system 606 (similar to drive system 200) is configured to cause translation of the second portion 602 relative to the first portion 600. In particular examples, an entirety of the drive system 606 is contained within the internal distraction component 604.

Similar to drive system 200 (FIG. 1), the drive system 606 can include a driver 608 and a gear system 610 coupled with the driver 608. In certain cases, the driver 608 is located axially between the gear system 610 and the first portion (or, plate) 600. In particular examples, the driver 608 is located between a proximal end 612 of the implant 100A and the gear system 610. According to certain implementations, a distal end 614 of the internal distraction component (e.g., distractor) 604 includes a first threaded coupler 616 for mating with a second threaded coupler 618 on the second portion 602. In some cases, actuation of the driver 608 engages the gear system 610 and initiates rotation of the first threaded coupler 616. In particular implementations, a majority of an axial extent (along axis (a)) of the first plate 600 overlaps an axial extent of the distractor 604, and a portion 620 of the first plate 600 overlaps with the distractor 604 when both the portion 620 of the first plate 600 and a portion 622 of the distractor 604 intersect a plane (P) perpendicular to the (axial) length of the distractor 604. As noted herein, the axial extent can refer to axial length, or length along the primary axis of distraction (a).

Figure 33:
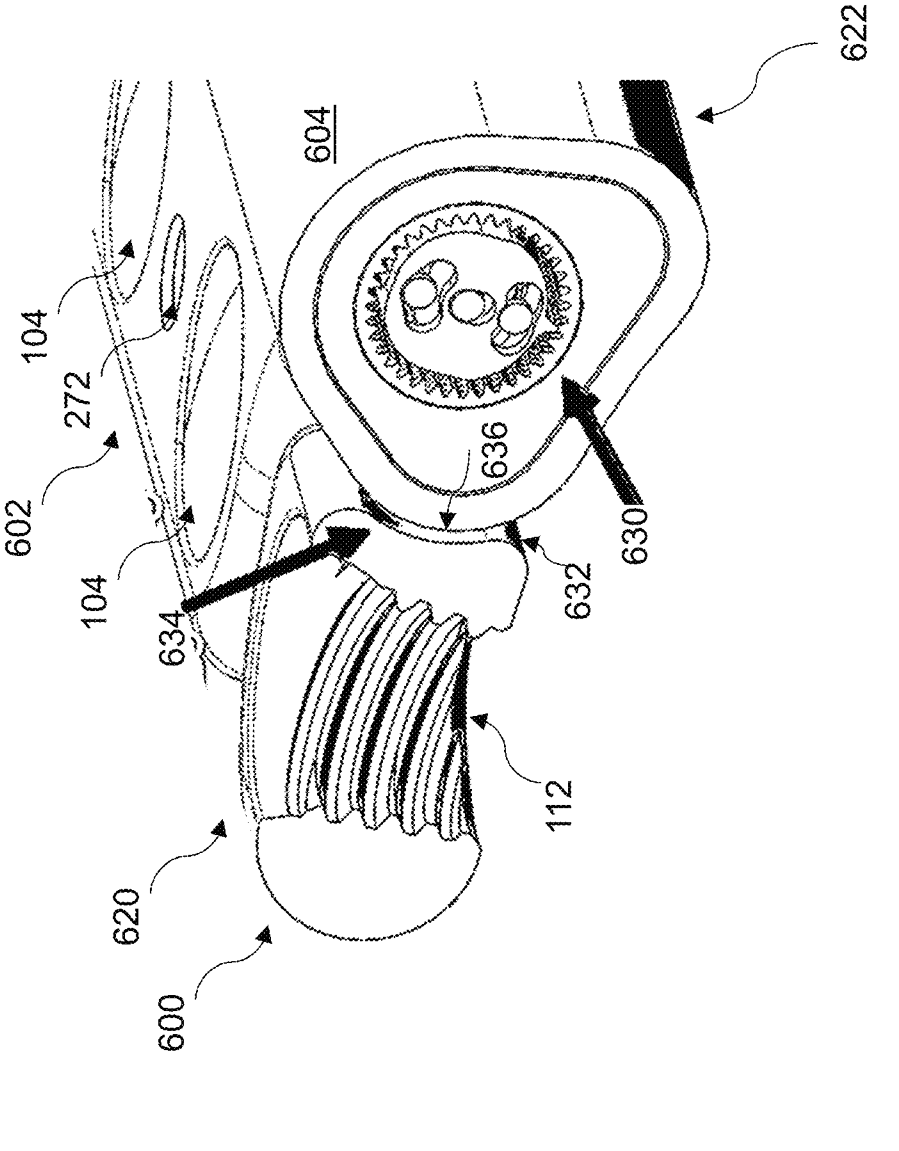
FIG. 33 is a partially cut-away view of a portion of the implant of FIGS. 31 and 32.

In further implementation, e.g., as illustrated in FIGS. 31 and 33, the implant 100 can further include a brake (e.g., “parking” brake) 630 located axially between the driver 608 and the gear system 610. The brake 630 can act to halt, or park, translation of the output driver 210. In particular cases, when the driver 608 is not being driven (e.g., caused to rotate) by an external device such as a magnetic actuator, a tooth in the brake 630 remains locked into the spring gear (e.g., via a spring) to restrict translation. When the driver 608 is actuated (e.g., turned by an external device), the brake 630 retracts and transmits axial force to the first planetary gear carrier, i.e., causing translation of the driver 210 and the implant 100A. In various implementations, the brake 630 is located in a section of the distractor 604 that has a non-circular cross-section, e.g., an oblong shape as illustrated in FIG. 33. In certain additional implementations, the portion 620 of the first plate 602 is separated from the distractor 604, e.g., defining a gap 632. In these cases, the gap 632 is defined between a first surface 634 of the portion 620 of first plate 602, and a second surface 636 of the distractor 604. In certain cases, the first surface 634 and second surface 636 are contoured to minimize the gap 632 therebetween. In particular cases, the first surface 634 and second surface 636 have similar profiles, and in more particular cases, have complementary shapes.

Figure 36:
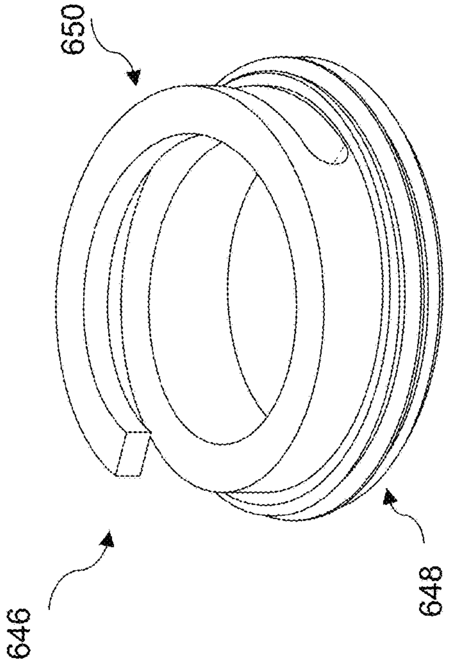
FIG. 36 shows a complementary portion of the anti-jam feature of FIG. 35.
Figure 37:
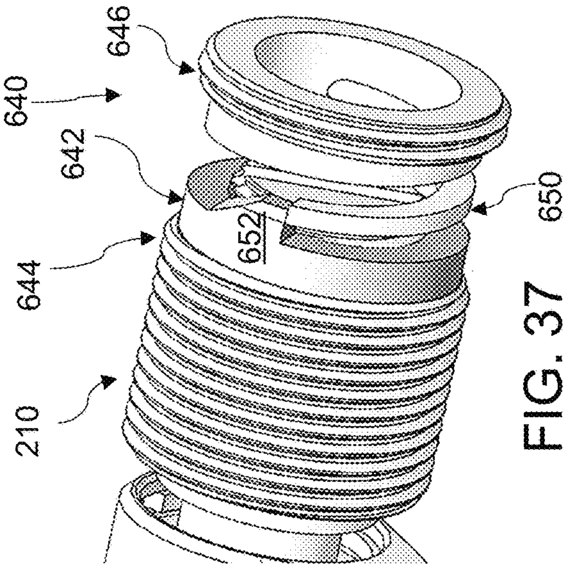
FIG. 37 shows the anti jam features of FIGS. 35 and 36 working in concert.
Figure 35:
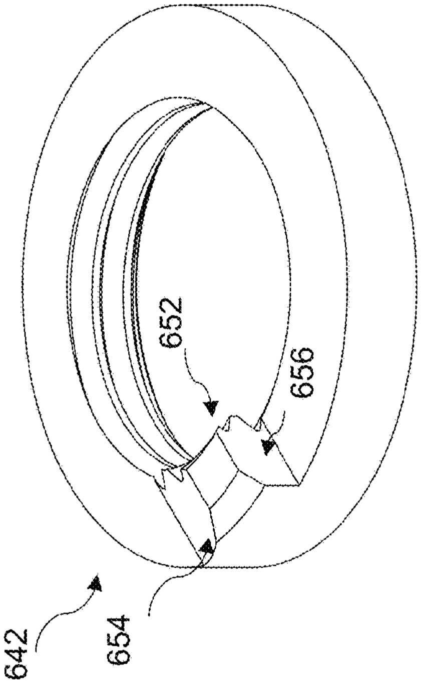
FIG. 35 shows a portion of an anti jam feature according to various embodiments of the disclosure.
Figure 34:
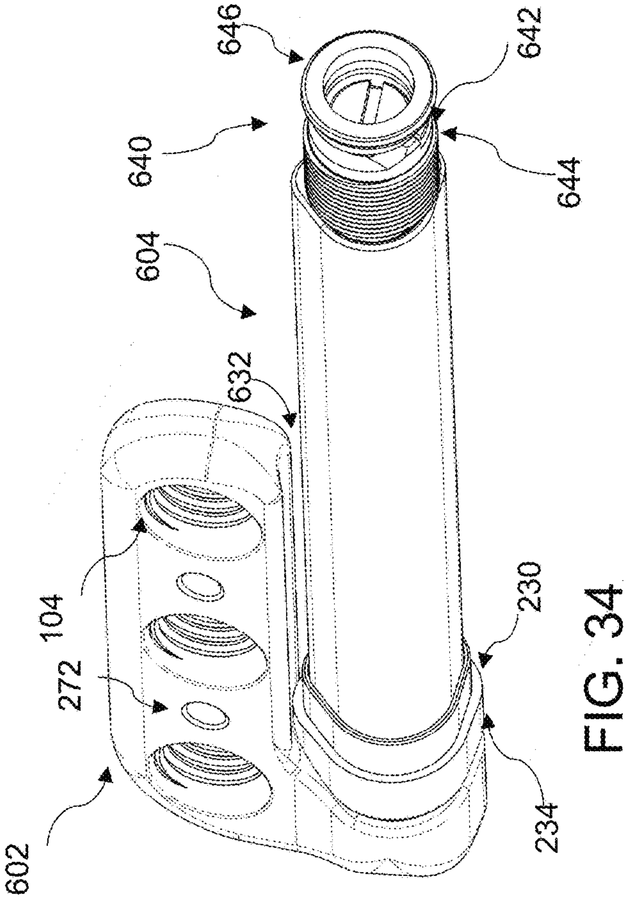
FIG. 34 is a perspective view of a portion of an implant according to various additional embodiments of the disclosure.

FIG. 34 shows the first portion 600 (e.g., first plate) and distractor 604 separated from the second portion (e.g., plate) 602, and illustrating an anti jam feature 640. The anti jam feature 640 is shown in parts in FIGS. 35 and 36. FIG. 35 illustrates a nut 642 that fits on the distal end 644 of output driver 210 (FIGS. 31, 34), and FIG. 36 illustrates an anti jam member 646 coupled with an internal surface of the second portion (plate) 602, e.g., to interact with the nut 642 in preventing jamming of the distractor 604. The anti-jam member 646 can include a threaded section 648 that is coupled with a complementary threaded section in the second portion (plate) 602, and a spiral section 650 (e.g., spiral cut section) that is configured to interface with an arm 652 on the nut 642. The spiral section 650 can include a slot that extends both axially and radially about the member 646. The spiral section 650 can provide a spring-type resistance to compressive force in the axial direction (a). In certain cases, the arm 652 has distinct profiles on opposite sides, e.g., a sloped profile 654 on a first side of arm 652 and a straight (normal) profile 656 on the opposite side of the arm 652. In these cases, the arm 652 is configured to rotate to engage the spiral section 650 with the straight profile 656 in a first (rotational) direction to mitigate jamming of the distractor 604. Interaction between arm 652 and spiral section 650 is illustrated in greater detail in FIG. 37.

As described herein with reference to implant 100 in FIG. 1, in certain cases, the sleeve 107 of the second plate 108 is sized to axially overlap the distractor 106. Among other features, the configuration of distractor 106 and second plate 108 (e.g., sleeve 107) can enable the implant 100 to be relatively compact when compared with conventional implants. Similar benefits are realized from the additional implementations of implant shown and described herein, e.g., implants 310, 320, 330 in FIGS. 12-14. Further, implant 100A (FIGS. 31-33) also has a beneficially compact configuration similar to implant 100 in FIG. 1, e.g., where sleeve 107 is sized to axially overlap distractor 604, and in certain cases, a portion of sleeve 107 axially overlaps portion 620 of the first plate 600 (e.g., where portion 620 includes one or more fixation aperture 104). With reference to both implant 100 (FIGS. 1, 2, 3) and implant 100A (FIGS. 31-33), in some examples, the implant 100, 100A is movable between a fully compact position PC (FIG. 32) and a fully extended position PE (FIG. 31). In certain implementations, a difference in length (i.e., axial length, along axis (a)) between the fully extended position PE and the fully compact position PC is approximately 45 millimeters (mm) to approximately 55 mm. In a more particular example, the difference between the fully extended position PE and the fully compact position PC is at least 50 mm. In certain examples, the axial length (La) of the implant 100 in the full compact position PC is approximately 75 mm to approximately 83 mm, and in more particular examples, approximately 78 to 79 mm. In certain examples, the axial length (La) of the implant 100 in the full extended position PE is approximately 125 mm to approximately 133 mm, and in more particular examples, approximately 128 to 129 mm.

As discussed above, implants described herein can include first and second portions (e.g., 600 and 602 of implant 100A) that are configured to be attached to a bone at various locations via one or more holes for receiving a bone anchor (e.g., screws, pins, blades, or nails). Different patients or surgeons may benefit from different configurations of portions, which may provide for different holes or configurations of holes. An implant or portions thereof can be configured for modular design to allow a user or manufacturer to customize implants.

In an example, modular components are fit together via a tapered and shaped wedge. For example, the wedge can have a cross-section that is rectangular, triangular, circular, oval, ellipsoid, peanut-shaped, or has the shape of a Cassini oval, other shapes, or combinations thereof. The components can then be press fit together.

FIGS. 38-55 illustrate example modular implants having different modules couplable thereto. For example, there may be a plurality of different fixation modules connectable to an implant body to give the implant different fixation capabilities. For instance, the fixation modules (e.g., a fixator) may come in different sizes and fixation aperture arrangements. The fixation modules can be provided as part of a kit and a user can select a particular fixation module for use with a particular patient or surgical scenario.

Figure 38A:
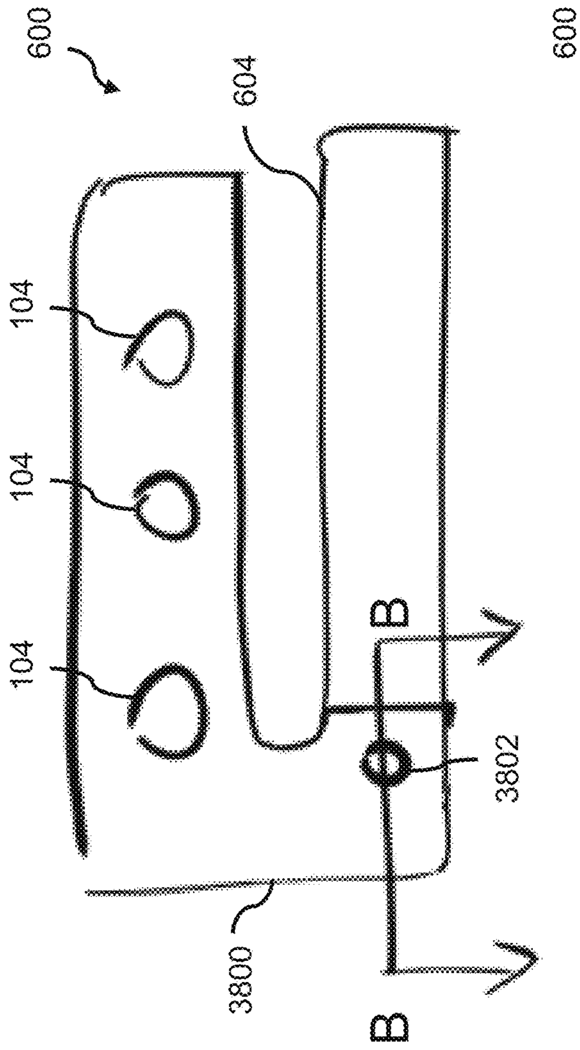
FIG. 38, which is made up of FIGS. 38A and 38B, shows an example of a first portion of an implant having modular capabilities according to various embodiments of the disclosure.
FIG. 38B is a cross section taken along line B-B in FIG. 38A.
Figure 38B:
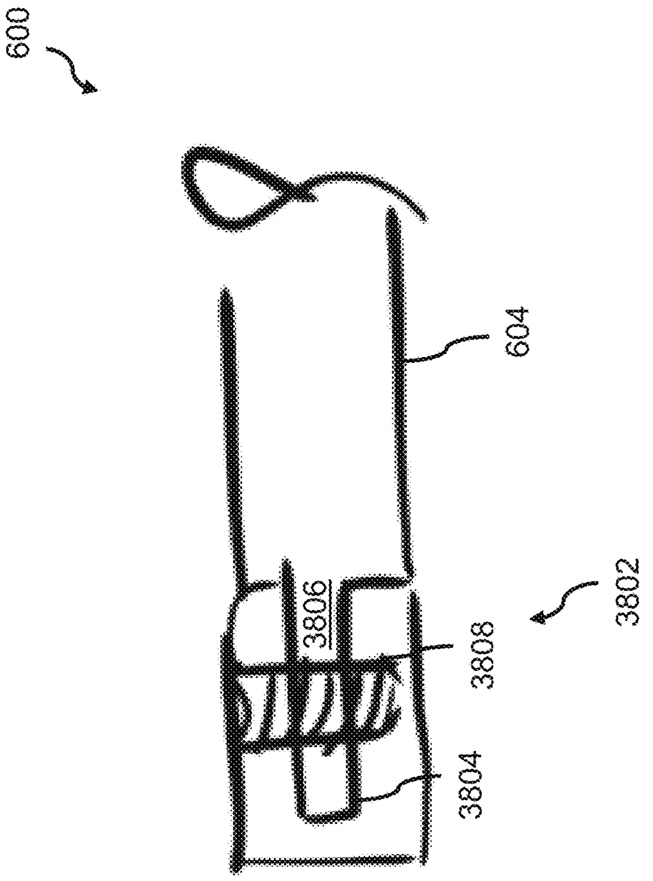

FIG. 38, which is made up of FIGS. 38A and 38B, shows an example of a first portion 600 (described in more detail above) of an implant having modular capabilities. FIG. 38B is a cross section taken along line B-B in FIG. 38A. The first portion 600 includes a distractor 604 coupled to a fixation module 3800. The fixation module 3800 includes one or more fixation apertures 104. The fixation module 3800 is a fixation component (e.g., a plate) that can be a module couplable with an implant (e.g., a distractor thereof). For instance, the implant can be modular such that a plurality of different fixation modules 3800 can be coupled to the modular implant to change the implant's capabilities (e.g., fixation capabilities). The fixation module 3800 is coupled directly to the distractor 604 via an attachment 3802. As illustrated, the attachment 3802 includes a mortise 3804 and tenon 3806 connection held together with a set screw 3808. In other implementations, the attachment 3802 can take other forms. The attachment 3802 can permit an assembler (e.g., preoperatively or intraoperatively) to swap out different modular components 3800 to better fit a patient.

Figure 39:
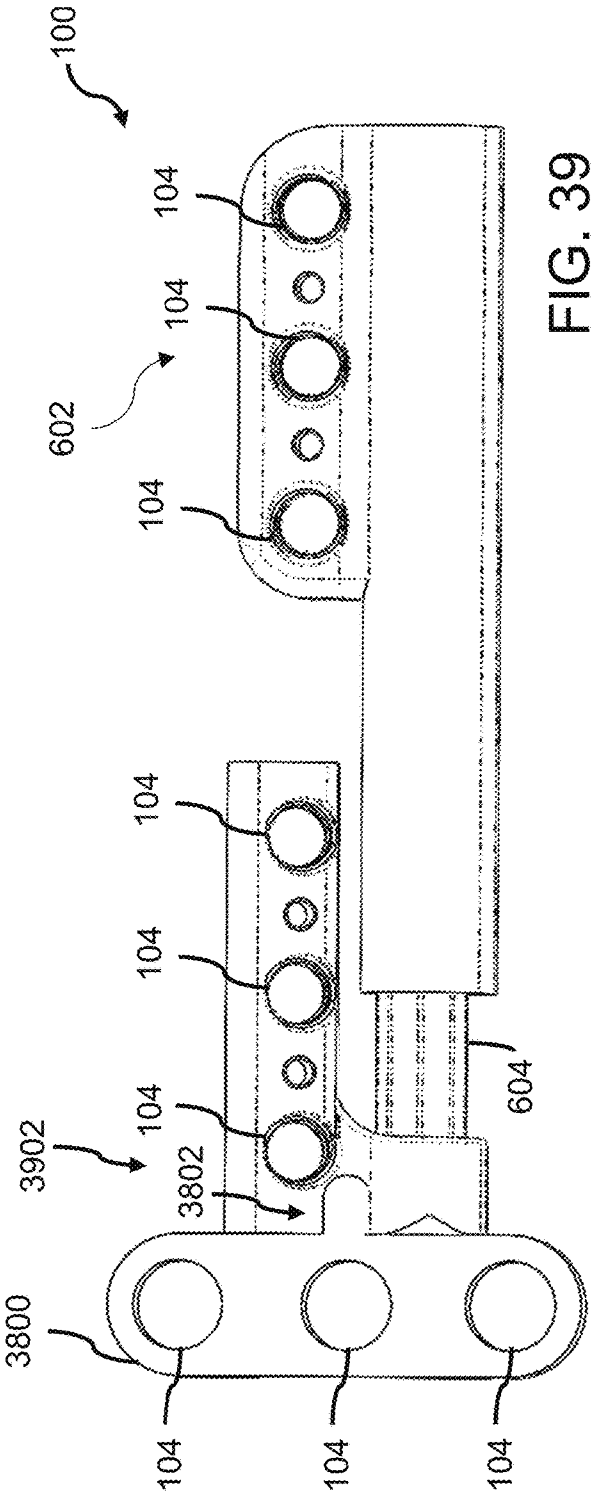
FIG. 39 illustrates an implant having a first example fixation module coupled to a distractor via an intermediary component, according to various embodiments of the disclosure.
Figure 40:
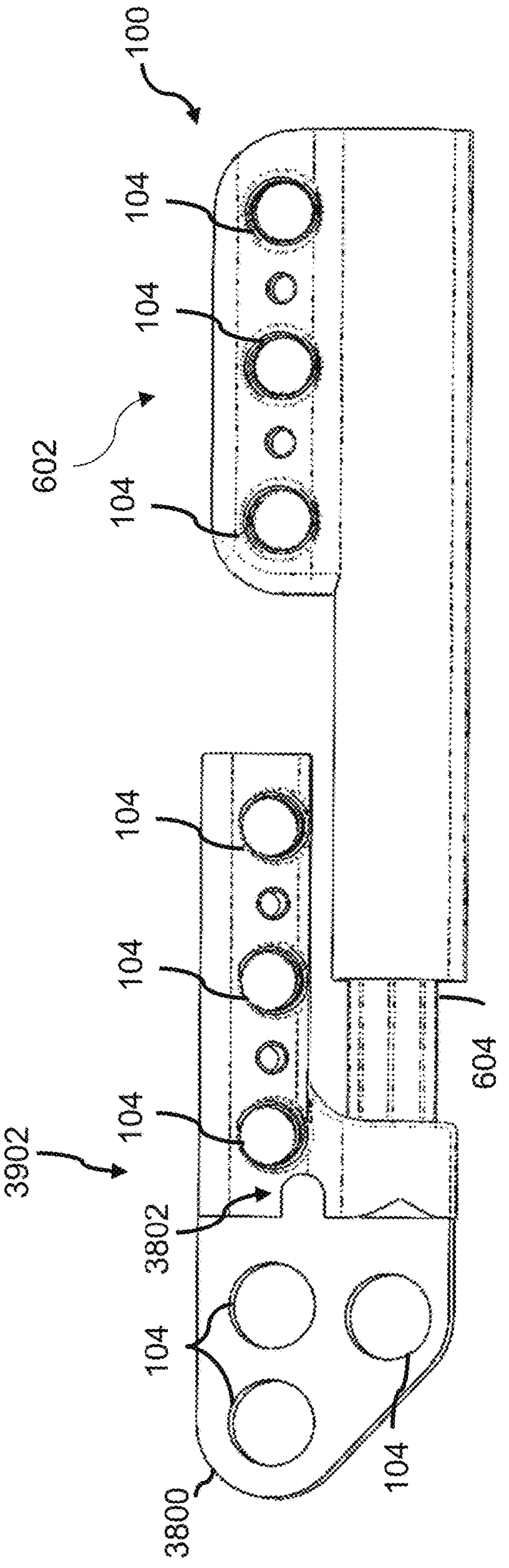
FIG. 40 illustrates an implant similar to that of FIG. 39, but with a second modular component.
Figure 41:
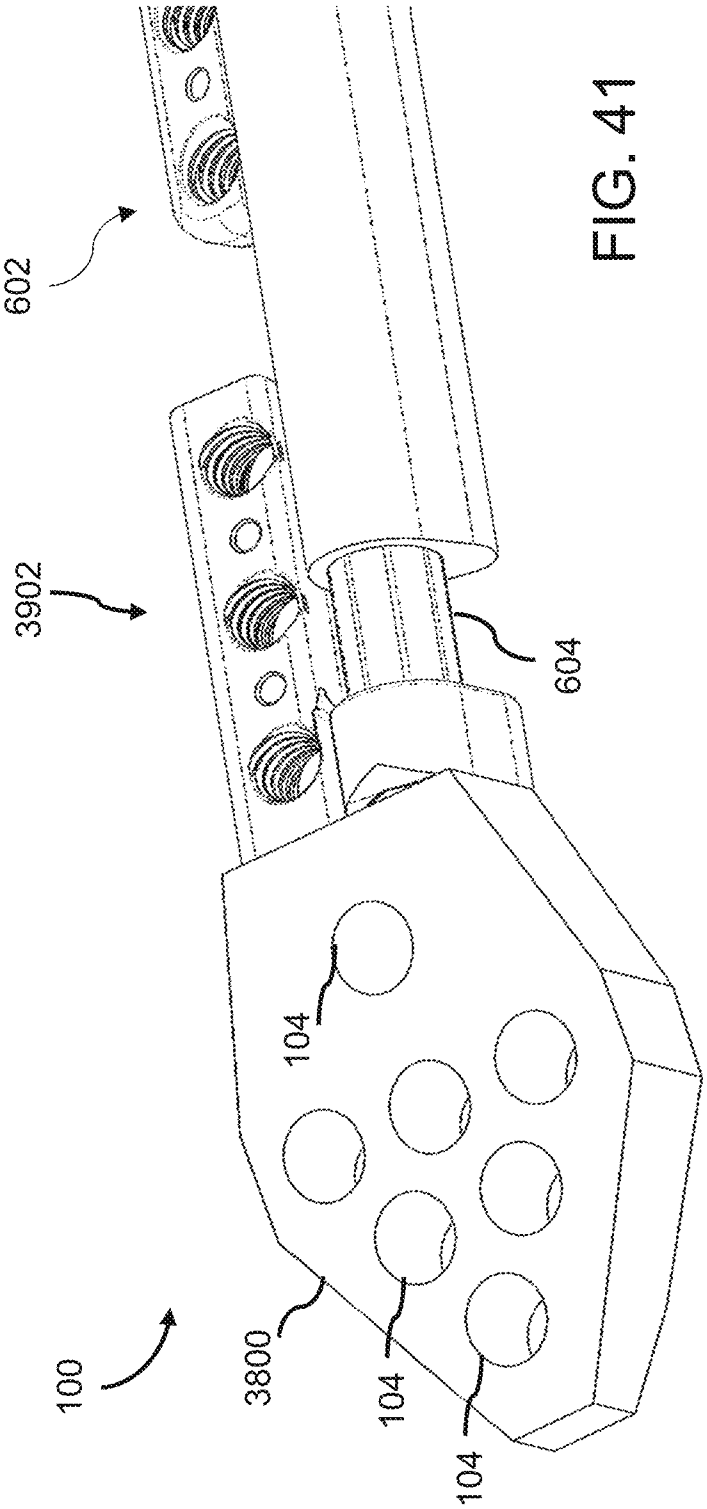
FIG. 41 illustrates an implant similar to that of FIG. 39, but with a third modular component.

FIGS. 39-41 illustrate additional example implants 100. FIG. 39 illustrates an implant having a first example fixation module 3800 coupled to a distractor 604 via an intermediary component 3902. Here, the intermediary component 3902 has a similar shape to the first plate (600, above) with one or more fixation apertures 104. An attachment 3802 is formed between the fixation module 3800 and the intermediary component 3902. The attachment 3802 can take any of a variety of forms, such as the configuration described in FIG. 38. In the illustrated example of the first example modular component 3900 includes at least two fixation apertures 104 extending along a line extending perpendicular to the length of the implant 100. The first example modular components 3900 include lobes that extend beyond a maximum width of the intermediary component 3902.

FIG. 40 illustrates an implant 100 similar to that of FIG. 39, but with a second modular component 3800. The second fixation module 3800 includes three fixation apertures 104 in a triangular arrangement. In this example, the triangular arrangement is a right triangle with two of the apertures 104 along a line that also passes through the apertures 104 of the intermediary component and with two of the apertures 104 along a line that passes along the distractor 604. In other examples, the two apertures are along a line that passes along the distractor 604 and only one aperture is on a line that passes through the apertures 104 of the intermediary component 3902.

Figure 44:
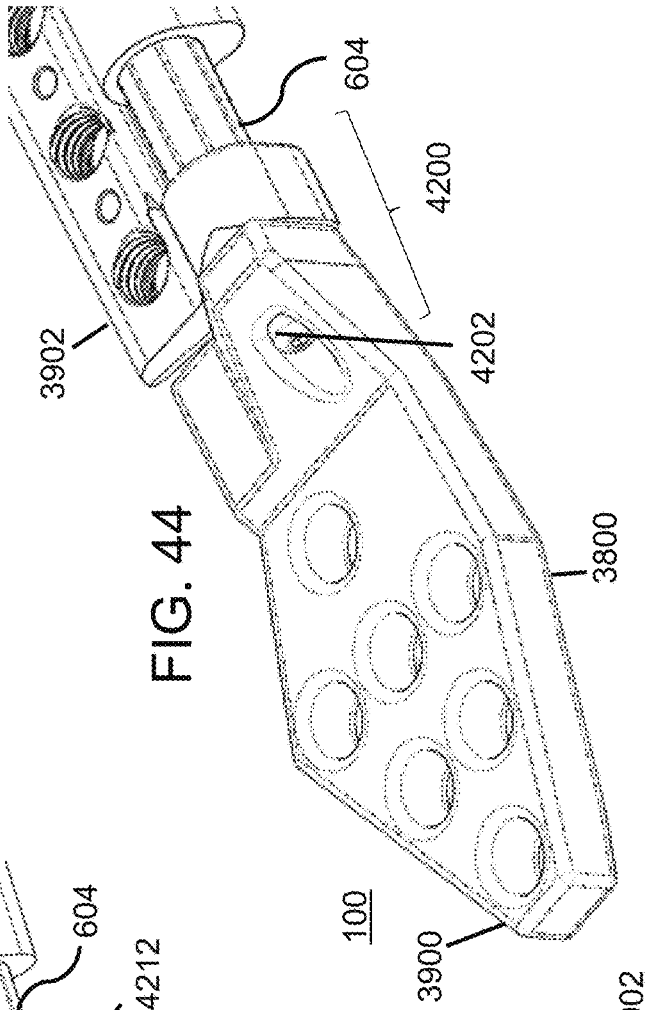
FIG. 44 illustrates a perspective view of an implant and attachment component according to various embodiments of the disclosure.
Figure 42:
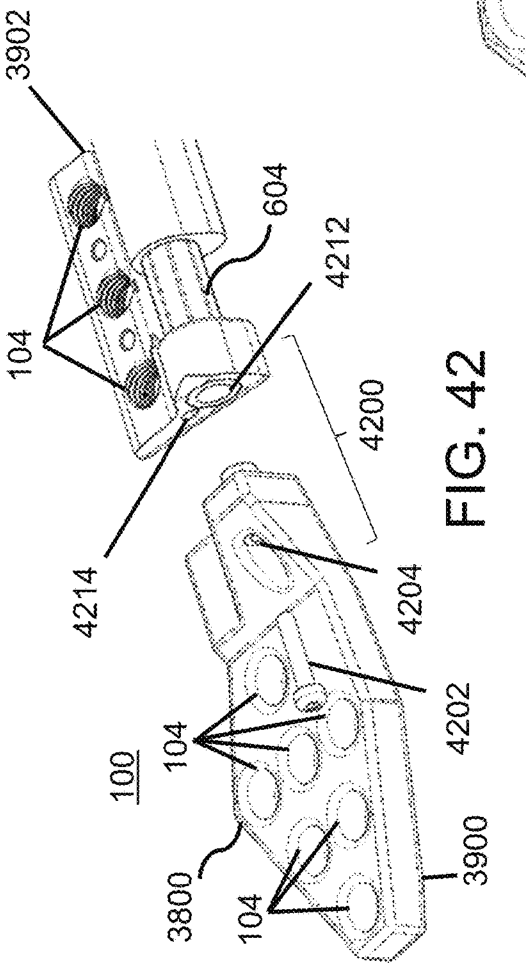
FIG. 42 illustrates a perspective view of an implant in an exploded state according to various embodiments of the disclosure.
Figure 43:
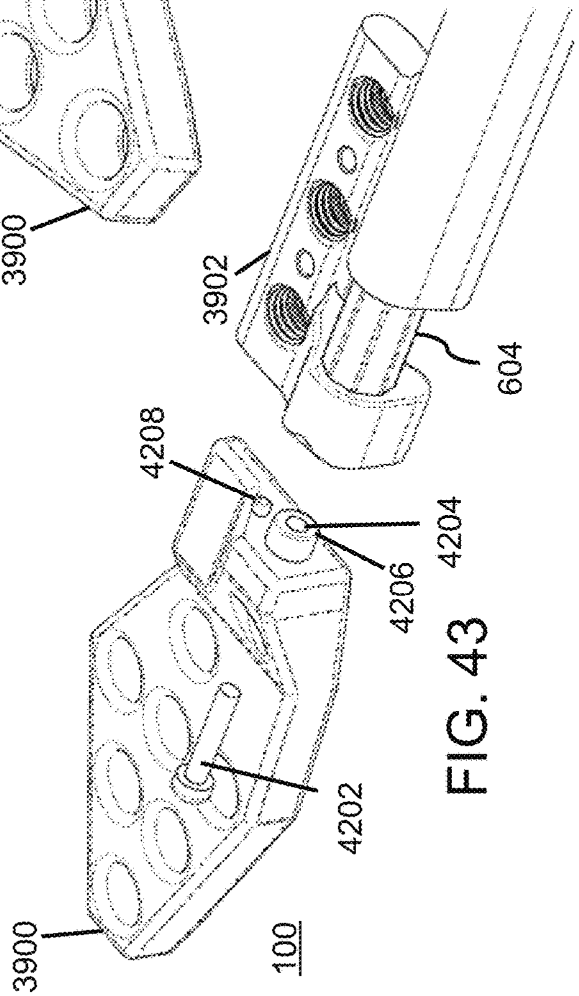
FIG. 43 illustrates a perspective view of an implant in an exploded state according to various embodiments of the disclosure.

FIG. 41 illustrates an implant 100 similar to that of FIG. 39, but with a third modular component 3900. The third modular component 3900 includes a plurality of fixation apertures 104 in a so-called "cobra head" arrangement. FIGS. 42-44 illustrate partial perspective views of an implant 100 having a fixation module 3800 coupled to an intermediary component 3902 via an attachment 4200. In particular, FIGS. 42 and 43 illustrate perspective views of the implant 100 in an exploded state. FIG. 44 illustrates a perspective view of the implant 100 in an assembled state. In this example, the modular component 3900 includes a plurality of fixation apertures 104 in a cobra head arrangement, but the techniques can be applied in any of a variety of arrangements. In this example, the attachment includes an axial screw 4202 that fits through a first opening 4204 of the fixation module 3800 and into a second opening 4212 of the intermediary component 3902. As illustrated, the first opening 4204 extends through a tapered boss 4206 (e.g., a 3 degree taper). The boss 4206 can facilitate alignment with the second opening 4212. The second opening 4212 can be threaded, such that the axial screw 4202 can thread into the threads of the second opening 4212 to secure the modular component 3800. The screw 4202 can be axial in that it is coaxial with the length of the distractor 604. As illustrated, the second opening 4212 is part of the intermediary component 3902, but it need not be. For example, the second opening 4212 can be part of the distractor 604 or another component. The attachment 4200 can include an alignment pin 4206 that fits into an alignment opening 4214 to facilitate alignment and stability. As illustrated, the alignment pin 4208 extends from the fixation module 3800 and the alignment opening 4214 is defined by the intermediary component 3902.

Figure 45:
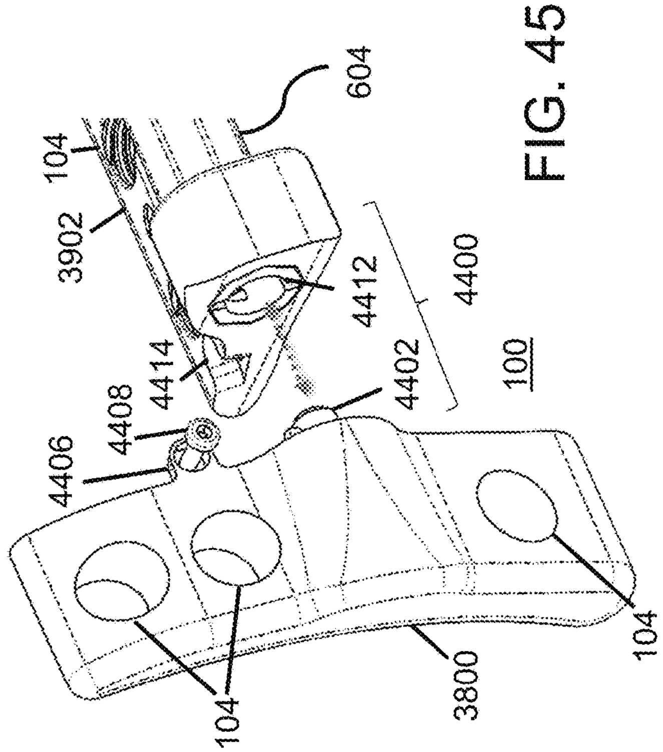
FIG. 45 illustrates a perspective view of aligning separate portions of the attachment to connect the fixation module and the intermediary component, according to various embodiments of the disclosure.
Figure 46:
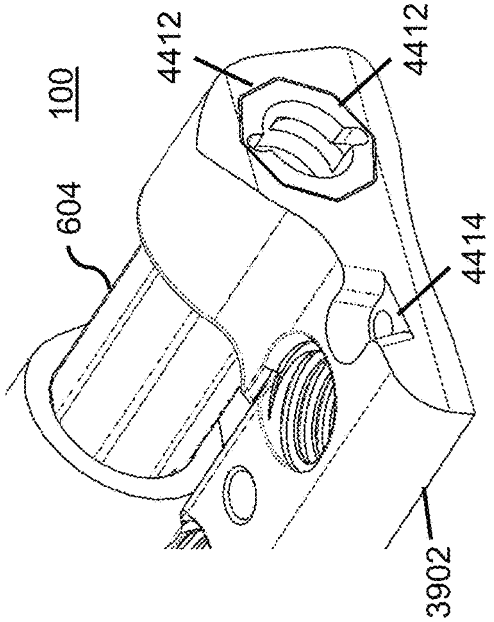
FIG. 46 illustrates a perspective view of the attachment components of the intermediary component (or the distractor) according to various embodiments of the disclosure.
Figure 47:
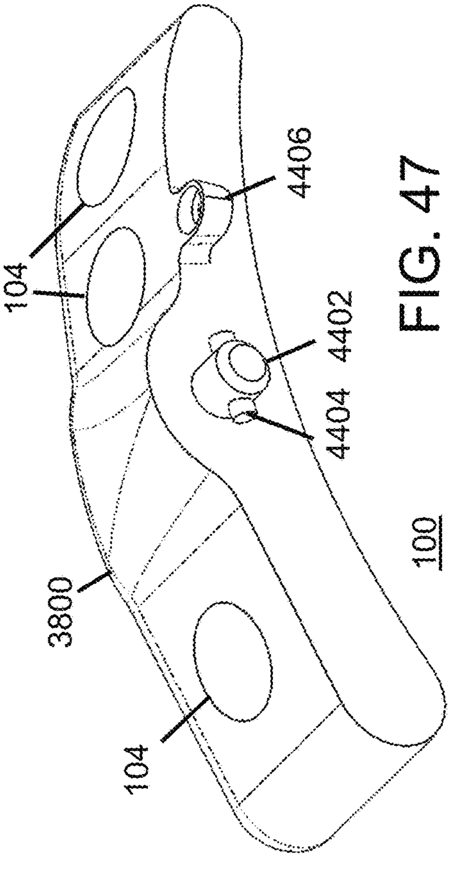
FIG. 47 illustrates a perspective view of the modular component according to various embodiments of the disclosure.
Figure 48:
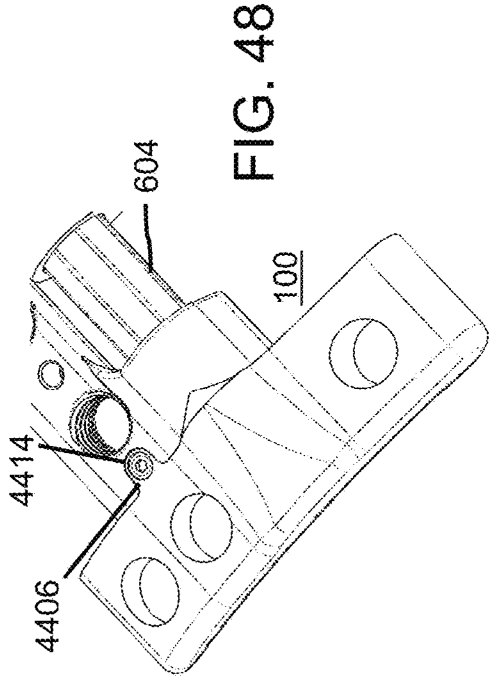
FIG. 48 illustrates a perspective view of the combined implant according to various embodiments of the disclosure.
Figure 50:
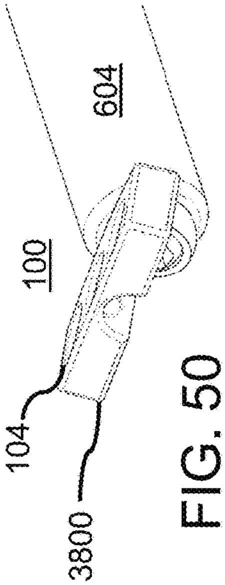
FIGS. 50-53 illustrate perspective views of example articulations of the implant of FIG. 49.
Figure 51:
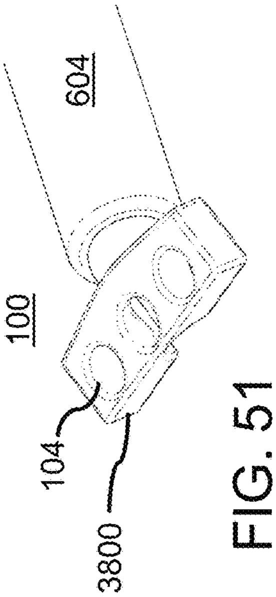
Figure 52:
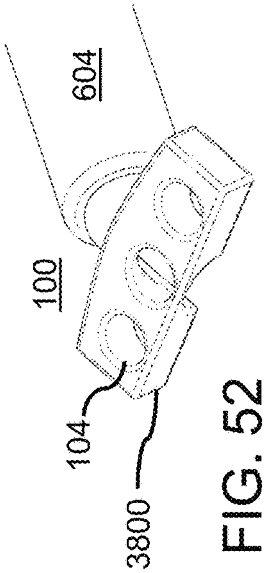
Figure 53:
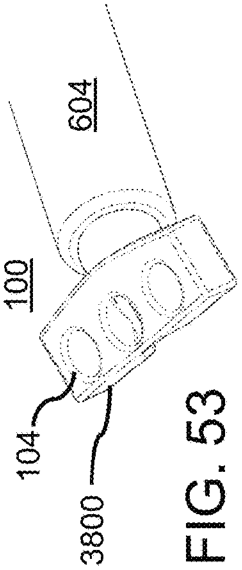

FIGS. 45-48 illustrate perspective views of an implant 100 having a fixation module 3800 coupled to an intermediary component 3902 via an attachment 4400. FIG. 45 illustrates a perspective view of aligning separate portions of the attachment 4400 to connect the fixation module 3800 and the intermediary component 3902. FIG. 46 illustrates a perspective view of the attachment 4400 components of the intermediary component 3902 (or the distractor 604). FIG. 47 illustrates a perspective view of the modular component 3800. FIG. 48 illustrates a perspective view of the combined implant 100.

The attachment 4400 includes a protrusion 4402 in the form of a pin-and-shank-sleeve coupling configured to fit into a complimentary receiver 4412. As illustrated, the protrusion 4402 extends from the modular component 3800, and the complimentary receiver 4412 is a portion of the intermediary component 3902 or the distractor 604. The protrusion 4402 includes a pin 4404 extending substantially perpendicular therefrom. The complimentary receiver 4412 can have a cross sectional shape that is configured to provide a complementary fit with a cross sectional shape of a portion of the protrusion 4402 and pin 4404. For example, the receiver 4412 can include an opening having a cross sectional shape configured to matingly receive the protrusion 4402 and the pin 4404 therein. The pin 4404 can be disposed at a point along the axial extent of the protrusion 4402, such that in use, the end of the protrusion 4402 can be inserted into or withdrawn from the receiver 4412 regardless of rotational orientation, but insertion of the pin 4404 and the portion of the protrusion 4402 beyond the pin 4404 requires rotational alignment of the pin 4404 with the profile of the opening of the receiver 4412. With the pin 4404 and the receiver 4412 aligned, the protrusion 4402 and the pin 4404 can be inserted into the receiver 4412. Once inserted, the fixation module 3800 can be rotated relative to the rest of the implant, thereby causing the pin 4404 to rotate out of alignment. With the pin 4404 out of alignment, the fixation module 3800 is thereby coupled with the rest of the implant 100. The attachment 4400 can be configured such that alignment of the pin 4404 and the receiver 4412 is not typical in an as-implanted form of the implant 100. For example, as shown in FIG. 45, the pin 4404 is aligned with the receiver 4412, so that insertion can be achieved, but the fixation module 3800 is rotated in a way that would interfere with proper implantation. FIG. 48 by contrast shows the implant 100 in a more typical as-implanted form, but in this form the pin 4404 is out of alignment and the fixation module 3800 is coupled. In the illustrated example, the fixation module 3800 is rotated by 90 degrees to move from the position in FIG. 45 to the position in FIG. 48.

As illustrated, the attachment 4400 can further include a tab 4406 extending from one component that fits within a cutout 4414 within another component. The tab 4406 and cutout 4414 can be secured by a screw 4408. These can be supplementary attachment structures that are engaged after the attachment via the pin 4404 and receiver 4412 is complete.

The fixation module 3800 can take any of a variety of forms. In this instance, the fixation module 3800 is generally perpendicular to the length of the implant 100. In addition the fixation module 3800 has a curved bottom profile. The fixation module 3800 further includes a portion with an exaggerated curvature to match a curvature of the intermediary portion 3902.

Figure 49:
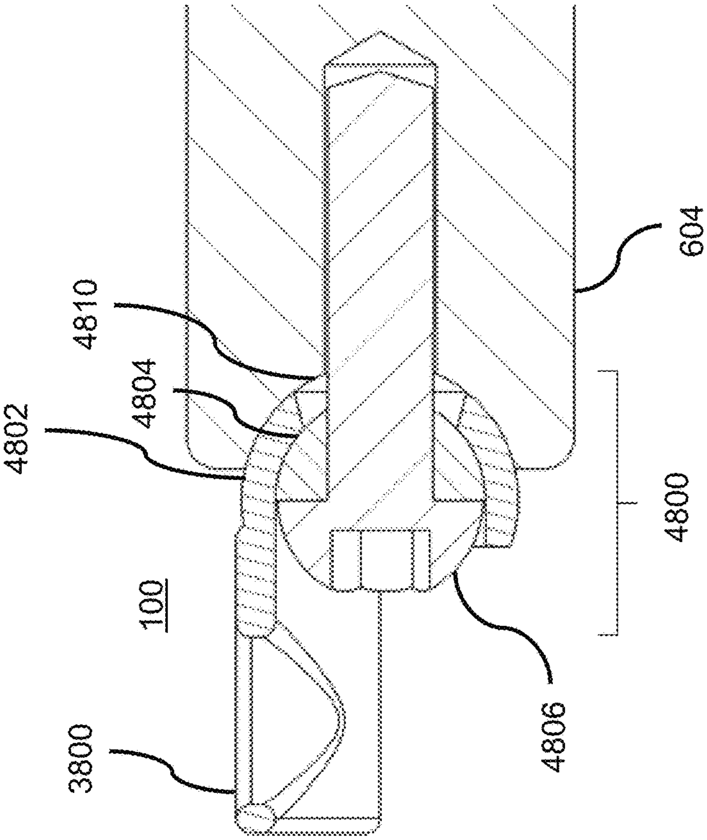
FIG. 49 illustrates a cross-section view of an implant according to various embodiments of the disclosure.

FIGS. 49-53 illustrate a first example implant 100 with an articulable modular component 3800. The fixation module 3800 includes fixation apertures 104. FIG. 49 illustrates a cross-section view of an implant 100. The fixation module 3800 is connected to the distractor 604 (or an intermediary component) with an attachment 4800 that permits angular adjustment of the fixation module 3800 relative to the distractor 604. As illustrated, the angular adjustment is facilitated between an interaction between a spherical boss 4802 coupled to the fixation module 3800 and a spherical bowl 4810 of the distractor 604. The boss 4802 and the spherical bowl 4810 can be linked by a spherical head screw 4806 and an optional washer 4804. The connection can be such that the head screw 4806 extends axially to the distractor 604. The connection can be such that the fixation module 3800 can be move to a desired angle or position and then tightened. The connection can be such that there are at least three degrees of freedom (e.g., pitch, roll, and yaw). FIGS. 50-53 illustrate perspective views of example articulations of the fixation module 3800 relative to the distractor 604.

Figure 54:
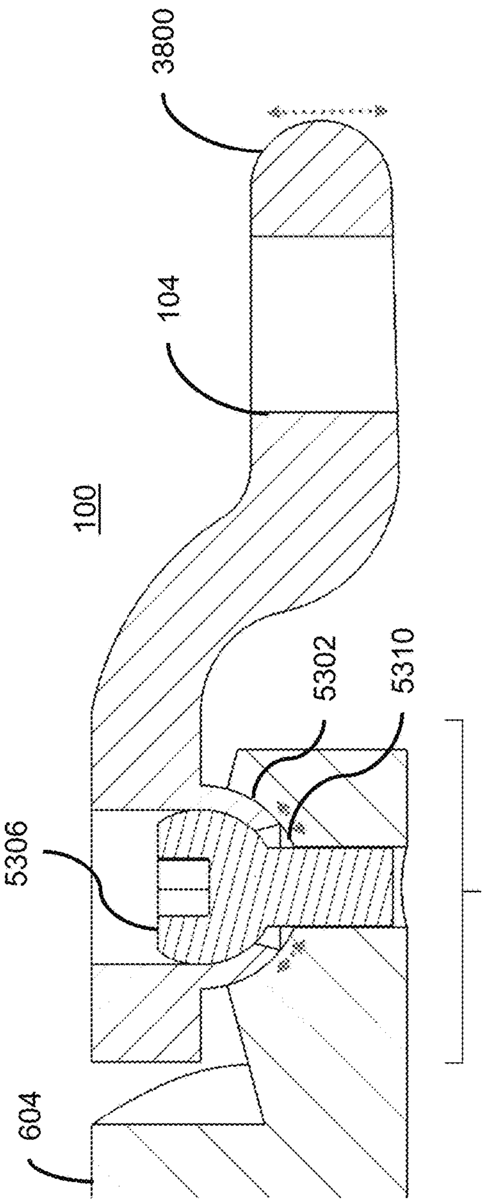
FIGS. 54 and 55 illustrate an example implant with an articulable modular component according to various embodiments of the disclosure.
Figure 55:
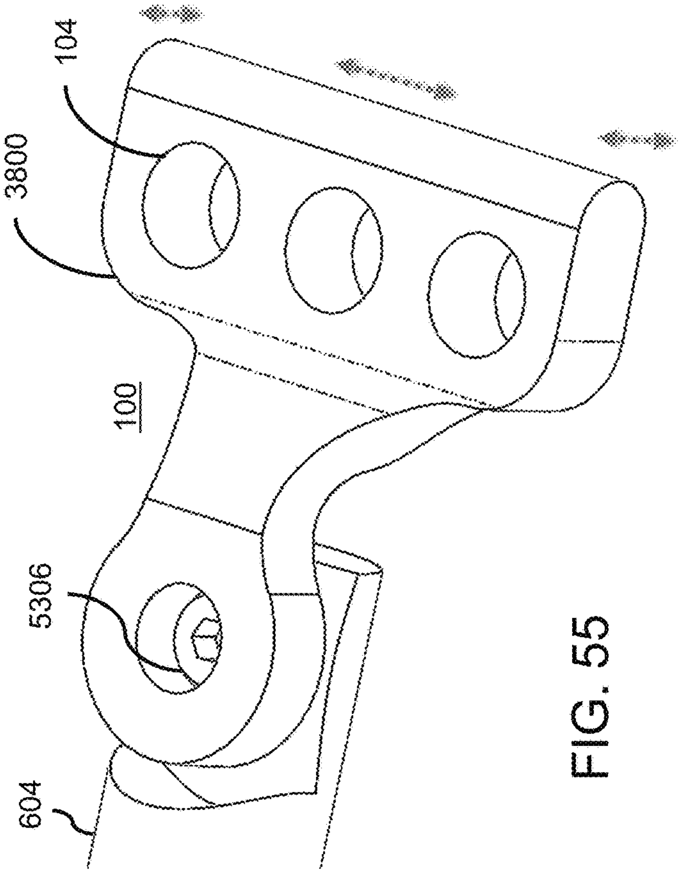

FIGS. 54 and 55 illustrate an example implant 100 with an articulable modular component. The fixation module 3800 includes fixation apertures 104. The fixation module 3800 is connected to the distractor 604 (or an intermediary component) with an attachment 5300 that permits angular adjustment of the fixation module 3800 relative to the distractor 604. As illustrated, the angular adjustment is facilitated between an interaction between a spherical boss 5302 coupled to the fixation module 3800 and a spherical bowl 5310 of the distractor 604. The boss 5302 and the spherical bowl 5310 can be linked by a spherical head screw 5306 and an optional washer. The connection can be such that the head screw 5306 extends perpendicular to the distractor 604. The connection can be such that the fixation module 3800 can be moved to a desired angle or position and then tightened. The connection can be such that there are at least three degrees of freedom (e.g., pitch, roll, and yaw).

It is noted that any portion of the implants (e.g., implants 100, 100A, 310, 320, 330) shown or described herein can be formed separately and subsequently combined, or may be formed collectively, such as integral parts. For example, the distractors (and associated shafts), sleeves, and/or plates described herein can be formed integrally with one another and/or can be formed separately and later combined. In some cases, driving components such as the driver 202 can be assembled in a distractor such as distractor 106 or distractor 604 with a cap to account for any differences in diameter between the internal housing of the distractor and the driver. Additionally, any components shown and described with reference to implants herein can be formed of a low-friction material to aid in adjustment of components relative to one another.

Various implementations enable displacement of bone in a patient's body, and provide compact and effective adjustment mechanism. The implants disclosed herein can enable treatment of bones with relatively smaller lengths than certain conventional implants that have a greater size (e.g., axial size). Additional features such as distraction loss mechanism(s) and anti-jam feature(s) (among others) can enhance reliability of the implants and aid in adjusting smaller-length bone with fewer procedural complications. Further, implants having modularity such as those disclosed according to various implementations can provide intraoperative flexibility.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

We claim:

1. A biocompatible implant for moving bone in a patient's body, the implant comprising:

a first plate configured to be attached to bone at a first location;

a second plate configured to be attached to bone at a second location;

a distractor extending from the first plate and being at least partially contained within the second plate; and at least one anti-rotation feature that includes one or more anti-rotation pegs extending radially from the distractor and one or more corresponding grooves in the second plate, wherein the distractor houses a drive system including a driver and a gear system coupled with the driver, and wherein the drive system is configured to cause translation of the second plate relative to the first plate.

2. The biocompatible implant of claim 1, wherein the driver is located axially between the gear system and the first plate.

3. The biocompatible implant of claim 1, wherein the driver is located between a proximal end of the implant and the gear system, wherein a distal end of the distractor includes an output driver for mating with an input driver on the second plate, wherein actuation of the driver engages the gear system and initiates rotation of the output driver, and wherein the implant further comprises at least one anti-rotation feature at an interface between the distractor and the second plate that, during actuation of the driver resists rotation of the second plate.

4. The biocompatible implant of claim 3, wherein the at least one anti-rotation feature includes a set of grooves on the second plate configured to resist rotation of a first set of grooves on the distractor.

5. The biocompatible implant of claim 3, wherein the at least one anti-rotation feature includes one or more straight surfaces at the interface between the second plate and the distractor.

6. The biocompatible implant of claim 1, wherein the one or more anti-rotation pegs includes a notch at each axial end thereof.

7. The biocompatible implant of claim 1, further comprising an end cap on a proximal end of the distractor for limiting an extent of translation of the second plate relative to the first plate.

8. The biocompatible implant of claim 7, further comprising a retaining ring extending at least partially circumferentially about the distractor, wherein the retaining ring is located axially between the end cap and the first plate.

9. The biocompatible implant of claim 1, wherein an entirety of the drive system is contained within the distractor.

10. The biocompatible implant of claim 1, wherein the distractor has an outer dimension with a non-circular cross-section and wherein the second plate has an inner dimension with a non-circular cross-section.

11. The biocompatible implant of claim 10, wherein the non-circular cross-section of the outer dimension of the distractor and the non-circular cross-section of the inner dimension of the second plate cooperate to limit rotation of the second plate during actuation of the drive system.

12. The biocompatible implant of claim 10, further comprising an anti-jam feature internal to the second plate.

13. The biocompatible implant of claim 1, further comprising a brake located axially between the driver and the gear system.

14. The biocompatible implant of claim 1, wherein:

the first plate includes a first housing substantially containing the distractor and a first connecting plate extending from the first housing, the first connecting plate including a first set of one or more holes for receiving a bone anchor;

the second plate includes a second housing including a sleeve and a second connecting plate extending from the sleeve, the second connecting plate including a second set of one or more holes for receiving a bone anchor, and wherein the sleeve is sized to axially overlap the distractor.

15. The biocompatible implant of claim 1, wherein a majority of an axial extent of the first plate overlaps an axial extent of the distractor, and wherein a portion of the first plate overlaps with the distractor when both the portion of the first plate and a portion of the distractor intersect a plane perpendicular to a length of the distractor.

16. The biocompatible implant of claim 1, wherein the driver includes at least one of:

a magnetic driver configured to be actuated by a controller external to the patient's body, an electric driver configured to be driven by an actuator in an external control device from a location external to the patient's body, or an ultrasound powered driver configured to be driven by an actuator in an external control device from a location external to the patient's body.

17. A biocompatible implant for moving bone in a patient's body, the implant comprising:

a first portion configured to be attached to a bone at a first location;

a second portion configured to be attached to the bone at a second location; and an internal distraction component extending from the first portion and at least partially contained within the second portion, the internal distraction component housing a drive system configured to cause translation of the second portion relative to the first portion, wherein an entirety of the drive system is contained within the internal distraction component, wherein the drive system includes a gear system coupled to a driver, wherein the driver is located between a proximal end of the implant and the gear system, and wherein a distal end of the internal distraction component includes a first threaded coupler for mating with a second threaded coupler on the second portion.

* * * * *